US012766085B2

(12) United States Patent
Cebrián Puche et al.

(10) Patent No.: US 12,766,085 B2
(45) Date of Patent: Oct. 20, 2026

(54) EMULSIFIER COMPOSITION FOR PERSONAL CARE FORMULATION

(71) Applicant: Lubrizol Advanced Materials, Inc., Cleveland, OH (US)

(72) Inventors: Juan Cebrián Puche, Barcelona (ES); Laure Dupin, Corbera de Llobregat (ES); Josep Lluís Viladot Petit, Barcelona (ES); Pedro Guardeño Mingueza, Barcelona (ES); Mariona Casanovas Gassó, Barcelona (ES)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 813 days.

(21) Appl. No.: 18/018,663

(22) PCT Filed: Jul. 30, 2021

(86) PCT No.: PCT/IB2021/056965

§ 371 (c)(1),
(2) Date: Jan. 30, 2023

(87) PCT Pub. No.: WO2022/029579

PCT Pub. Date: Feb. 10, 2022

(65) Prior Publication Data

US 2023/0301898 A1 Sep. 28, 2023

(30) Foreign Application Priority Data

Aug. 5, 2020 (EP) .................................... 20382725

(51) Int. Cl.

| | |
|---|---|
| ***A61K 8/73*** | (2006.01) |
| ***A61K 8/06*** | (2006.01) |
| ***A61K 8/99*** | (2017.01) |
| ***A61Q 19/00*** | (2006.01) |

(52) U.S. Cl.

CPC .............. *A61K 8/731* (2013.01); *A61K 8/062* (2013.01); *A61K 8/064* (2013.01); *A61K 8/73* (2013.01); *A61K 8/99* (2013.01); *A61Q 19/00* (2013.01); *A61K 2800/10* (2013.01)

(58) Field of Classification Search

None

See application file for complete search history.

(56) References Cited

U.S. PATENT DOCUMENTS

| | | | | |
|---|---|---|---|---|
| 3,827,899 A * | 8/1974 | Zirlin et al. | .......... | A23L 29/262 106/162.8 |
| 4,427,681 A * | 1/1984 | Munshi | ................ | A61K 9/0095 514/718 |
| 9,828,493 B2 | 11/2017 | Tan et al. | | |
| 2004/0191326 A1* | 9/2004 | Reo | .................... | A61K 31/4439 424/490 |
| 2013/0102705 A1* | 4/2013 | Sabio | ...................... | B28C 7/161 524/5 |
| 2020/0345608 A1 | 11/2020 | Bouzeloc et al. | | |

FOREIGN PATENT DOCUMENTS

| | | | | |
|---|---|---|---|---|
| CN | 103987273 A | 8/2014 | | |
| CN | 105395423 A | 3/2016 | | |
| CN | 111417380 A | 7/2020 | | |
| DE | 103 51 859 A1 | 6/2005 | | |
| JP | 2007-238516 A | 9/2007 | | |
| WO | WO 2013/085809 * | 6/2013 | ............... | A23L 1/05 |
| WO | WO 2013/085809 A1 | 6/2013 | | |

OTHER PUBLICATIONS

Qu et al (IFEESD, 2016) (Year: 2016).*

Babbar et al (Curr Microbiol 52:287-292, 2006) (Year: 2006).*

Product Information Seorostm Overview; List of K Roidal products; CeolusTM Crystalline cellulose; Asahi Kaseo Corporation—unknown date, mentioned in foreign search report, 2 pages.

Capron, et al., "Surfactant-Free High Internal Phase Emulsions Stabilized by Cellulose Nanocrystals," Biomacromolecules, vol. 14, pp. 291-296 (2013).

Fujisawa, et al., "Nanocellulose-stabilized Pickering emulsions and their applications," Science and Technology of Advanced Materials, vol. 18, No. 1, pp. 959-971 (2017).

Kalashnikova, "New Pickering Emulsions Stabilized by Bacterial Cellulose Nanocrystals," Langmuir, vol. 27, pp. 2471-7479 (2011).

Oza, et al., "Microcrystalline cellulose stabilized emulsions", J. Dispersion Science and Technology, vol. 7, No. 5, pp. 533-561 (1986).

Santos, et al., "A comparison of microfluidization and sonication to obtain lemongrass submicron emulsions. Effect of diutan gum concentration as stabilizer", LWT—Food Science and Technology, vol. 114, No. 108424, 29 pages (2019).

Xie, et al., "Redispersible Pickering emulsion powder stabilized by nanocrystalline cellulose combining with cellulosic derivatives," Carbohydrate Polymers, vol. 213, pp. 128-137 ( 2019).

Xu, et al., "Effect of diutan microbial polysaccharide on the stability and rheological properties of O/W nanoemulsions formed with a blend of Span20-Tween20," Dispersion Science and Technology, vol. 39, No. 11, pp. 1644-1654 (2018).

* cited by examiner

*Primary Examiner* — Craig D Ricci

(74) *Attorney, Agent, or Firm* — Michael A. Miller

(57) ABSTRACT

An emulsifier composition includes microcrystalline cellulose; at least one biogum of microbial origin; and, optionally, at least one cellulose ether or derivative thereof. Emulsions and personal care formulations including the emulsifier composition, methods of preparing the emulsifier composition, and a method of using the emulsifier composition to stabilize an emulsion which includes an oil phase and a water phase are also described.

7 Claims, No Drawings

EMULSIFIER COMPOSITION FOR PERSONAL CARE FORMULATION

This application claims the priority of International Application PCT/IB2021/056965, filed Jul. 30, 2021, and EP 20382725.8, filed Aug. 5, 2020, from which the PCT application claims priority, the disclosures of which are incorporated herein by reference in their entireties.

FIELD OF THE INVENTION

The invention relates to an emulsifier composition suitable for use in the preparation of personal care formulations comprising a water phase and an oil phase. In particular, the emulsifier composition can be used to formulate personal care formulations comprising emulsions such as skin care and hair care preparations. The emulsifier composition has beneficial effects on the stability, rheology and consumer acceptance of said formulations. The invention extends to emulsions and personal care formulations comprising the emulsifier composition and methods of preparing the same. The invention also extends to the use of the emulsifier composition to stabilize an emulsion comprising an oil phase and a water phase.

BACKGROUND OF THE INVENTION

Emulsions are one of the most common types of formulation used in cosmetics/personal care formulations. An emulsion is a heterogeneous system which is a mixture of two or more liquids that would not normally mix, i.e., it is a mixture of two or more liquids that are immiscible or of limited miscibility. One of the liquids is distributed in another of the liquids in the form of fine droplets. These droplets form a dispersed phase in the other liquid. The other liquid is referred to as the continuous phase.

Emulsions include oil-in-water (O/W) or water-in-oil (W/O) emulsions. Oil-in-water (O/W) emulsions have water as a continuous phase and oil as a dispersed phase. Water-in-oil (W/O) emulsions have oil as a continuous phase and water as a dispersed phase.

Emulsions have the advantage of being able to act as vehicles for providing the skin with a large amount of lipids and liposoluble ingredients, leaving the skin feeling pleasant and, for example, smooth, soft and/or moisturized. However, emulsions are thermodynamically unstable systems and require stabilization by, for example, surfactants or polymers, to prevent separation of the phases over an extended period of time. However, most stabilizing ingredients are synthetic, or are surface-active molecules and so can disrupt the skin barrier. Also, there is a growing interest in the use of ingredients that are biodegradable and environment-friendly for consumer products, and, in particular, personal care products.

The use of biopolymers in the personal care industry is known. For example, natural polysaccharides can be used as rheology modifiers to adjust the viscosity of formulations.

Cellulose is the main component of primary cell wall of green plants and some algae, and it is the most abundant natural polymer in the world. Cellulose is widely used in the preparation of paper, food, pharmaceuticals, and cosmetics, for example. Cellulose is a polysaccharide consisting of a linear chain of several hundred to many thousands of glucose units.

Cellulose has four different morphologies, depending on the source and treatment of the cellulose. Naturally occurring cellulose is known as Cellulose I, and is found in most plant cell walls. Cellulose II is used for textiles and can be obtained by heating naturally occurring cellulose in the presence of strong alkalis. Cellulose III and Cellulose IV are less common and usually occur in combination with types I and II. Cellulose III is amorphous can be obtained by treatment of Cellulose I or Cellulose II with ammonia or amines. Cellulose IV can be obtained by treatment of Cellulose III with glycerol at high temperatures. When cellulose contains both crystalline and amorphous domains it is known as microfibrillated cellulose (MFC), sometimes also referred as nanofibrillated cellulose (NFC). The amorphous domains can be removed by using different processes such as reactive extrusion, enzymatic reaction, mechanical grinding, ultrasonication, steam explosion and acid hydrolysis with mineral acids like sulfuric acid, hydrochloric acid or hydrobromic acid. When this amorphous domain is removed this product has different properties than the native cellulose and it is known as microcrystalline cellulose (MCC) (also referred as nanocrystalline cellulose (NCC)).

MCC is well known in the cosmetic and pharmaceutical industries. It is generally used as an aqueous thickener, stabilizer, abrasive, absorbent, anti-caking agent, binder or bulking agent. MCC has also been proposed as an emulsion stabilizer in emulsions stabilized by solid fine particles [Fujisawa, et al., "Nanocellulose-stabilized Pickering emulsions and their applications," Science and Technology of Advanced Materials, 2017, vol. 18, no. 1, 959-971]. This type of emulsion is called a Pickering emulsion. Nevertheless, MCC alone as emulsion stabilizer has several drawbacks. For instance, a high shear force, applied using sonication or microfluidization, is required in order to decrease the size of oil droplet, which is needed to obtain stable emulsions. In an emulsion, the size of the oil droplet is a key factor in the emulsion stability. As lower the particle size, the better the stability. Moreover, high concentrations of MCC are required.

Kalashnikova, et al., discloses Pickering emulsions stabilized by bacterial cellulose nanocrystals (BCNs) [Kalashnikova, et al., "New Pickering Emulsions Stabilized by Bacterial Cellulose Nanocrystals," (2011) Langmuir, 27, 2471-7479]. The bacterial cellulose nanocrystals are prepared via hydrochloric acid hydrolysis of bacterial cellulose. Kalashnikova, et al., discloses Pickering emulsions formulated at a 30/70 ratio (O/W), with a 5 g/L suspension of BCN in the water phase. The application of shear using sonication is required, which makes this process very difficult to scale-up. Further, at BCN concentrations below 2 g/L, the oil and water phases separate and coalescence occurs by compression during the centrifugation process. Thus, high concentrations of BCN are required.

In Capron. et al., a sonication process is also required to stabilize a Pickering 10/90 O/W emulsion containing cellulose nanocrystals and NaCl [Capron, et al., "Surfactant-Free High Internal Phase Emulsions Stabilized by Cellulose Nanocrystals" (2013), Biomacromolecules, 14, 291-296]. The cellulose nanocrystals are obtained from cotton fibers by acid hydrolysis with sulfuric acid.

MCC has also attracted interest as an intermediate material for producing cellulose nanocrystals (CNC) via microfluidization; the cellulose nanocrystals are modified with carboxymethyl cellulose sodium (CNCC) to prepare redispersible *camellia* oil Pickering emulsions powder (CO-PEP) [J. Xie, et al., "Redispersible Pickering emulsion powder stabilized by nanocrystalline cellulose combining with cellulosic derivatives" (2019) Carbohydrate Polymers, 213, 128-137].

Oza, et al., discloses the use of Avicel® RC-591 MCC in 1:4 O/W emulsions [Oza, et al., "Microcrystalline cellulose stabilized emulsions" (1986) J. Dispersion Science and Technology, 7(5), 533-561]. However, at a MMC concentration of 0.5% (w/w), oil droplets coalesce (as a result of insufficient Avicel® in the system). Thus a higher concentration of MCC is needed, e.g., higher than 1% (w/w). High concentrations of cellulose can lead to a high residue level on the skin and this can produce a non-pleasant sensory effect due to the balling up of the residue. Moreover, MCC has low compatibility with conventional surfactants such as Tween® 80. For these reasons, MCC is not completely satisfactory as an emulsion stabilizer.

DE10351859A1 provides preparations for use with insect repellants containing O/W emulsions containing MCC and xanthan gum. DE10351859A1 discloses a concentration of MCC in the preparation of from 0.1 to 5% by weight, based on the total weight of the preparation. DE10351859A1 discloses a concentration of xanthan gum in the preparation of from 0.05 to 2.5% by weight, based on the total weight of the preparation. DE10351859A1 discloses insect repellents in the form of oils in concentrations of from 2 to 60% by weight, based on the total weight of the preparation.

Polysaccharides other than cellulose have also been proposed as co-emulsifiers in surfactant systems.

Xu, et al., discloses the effect of diutan microbial polysaccharide on the stability and rheological properties of oil-in-water nanoemulsions formed with a blend of Span®20-Tween®20 [Xu, et al., "Effect of diutan microbial polysaccharide on the stability and rheological properties of O/W nanoemulsions formed with a blend of Span20-Tween20", Journal of Dispersion Science and Technology, 2018, Vol. 39, No. 11, 1644-1654]. All the nano-emulsions prepared with diutan gum (concentrations ranging from 70 to 700 mg $L^{-1}$ (0.007-0.07%, w/w)) are more stable 30 days later, and there is no obvious creaming phenomenon. As the emulsifier content increases from 6.0% to 10%, the Polydispersity index (PDI) obtained in the size distribution measurement of nano-emulsions increases, i.e., the droplet size of the nano-emulsions becomes closer. However, the amount of surfactant required is high (i.e., at least 6%, w/w) and the maximum amount of water in the emulsion is 80% (w/w). High amounts of surfactants have an impact in the skin barrier function as well as having detrimental environmental effects.

In food industry, diutan gum has also been proposed as a stabilizer of emulsions of lemongrass essential oil comprising Appyclean™ 6552 as surfactant [Santos, et al., "A comparison of microfluidization and sonication to obtain lemongrass submicron emulsions. Effect of diutan gum concentration as stabilizer" (2019), LWT—Food Science and Technology 114]. The emulsions provided contain 5% (w/w) of oil and 0.5% (w/w) of Appyclean™ 6652 (tensioactive surfactant) and 0.2% (w/w) diutan gum, and are prepared by using high energy methods such as sonication or microfluidization. The emulsion system requires surfactant (i.e., tensioactive) and thus is a different emulsion system to a Pickering emulsion. Further, there is no disclosure of stabilizing O/W emulsions having high concentrations of oil.

Accordingly, there is a need to find new emulsion systems that are stable, and that are appropriate for use in personal care formulations. There is a need to provide an alternative to conventional emulsifiers used in personal care formulations. There is a need to find new emulsion systems that show improved stability over an extended period than other known emulsion systems. Also, there is a need to provide naturally derived emulsifiers. The present invention sets out to meet some or all of these needs and to solve some or all of the above-identified problems.

SUMMARY OF THE INVENTION

The invention provides an emulsifier composition comprising:

a) microcrystalline cellulose;

b) at least one biogum of microbial origin; and, optionally, c) at least one cellulose ether or derivative thereof.

Preferably, the emulsifier composition comprises from about 20 to about 90 wt % of microcrystalline cellulose; from about 10 to about 80 wt % of at least one biogum produced by microbial fermentation; and from about 0 to about 20 wt % of at least one cellulose ether or derivative thereof. The weight percentages are based on the total weight of the composition. It has been found that the emulsifier composition of the invention can be used to provide highly stable oil-in-water and water-in-oil emulsions. It is believed that the high stability is due to a synergy resulting from the combination of the microcrystalline cellulose and the at least one biogum and, when present, the at least one cellulose ether derivative. Further, the emulsifier composition of the invention enjoys the advantages of being of low irritability to the skin and of comprising natural ingredients. The emulsifier composition of the invention may be used to produce emulsions that can be used in personal care formulations, in particular.

Thus, in another aspect, the present invention provides an emulsion or a personal care formulation comprising:

i) a water phase;

ii) an oil phase; and iii) the emulsifier composition of the invention.

In another aspect, the invention provides a method of preparing an emulsion or a personal care formulation comprising an oil phase and a water phase, where the method comprises the step of mixing the emulsifier composition of the invention with the oil phase and the water phase. The method of preparing an emulsion or a personal care formulation may comprise the steps of:

i) dispersing the emulsifier composition of the invention into a water phase;

ii) stirring the oil phase into the water phase to form an emulsion; and, optionally, iii) adjusting the pH of the emulsion to lower than 7.

In another aspect, the invention provides a method of stabilizing an emulsion comprising an oil phase and a water phase, comprising a step of mixing the emulsifier composition of the first aspect of the invention with the oil phase and the water phase. The emulsion can be a personal care formulation as described above.

In a further aspect, the invention provides for the use of the emulsifier composition of the first aspect of the invention to stabilize an emulsion comprising an oil phase and a water phase. The emulsion can be a personal care formulation as described above.

DETAILED DESCRIPTION OF THE INVENTION

As used herein, the term "comprising", which is inclusive or open-ended and does not exclude additional unrecited elements or method steps, is intended to encompass as alternative embodiments, the phrases "consisting essentially of" and "consisting of" where "consisting of" excludes any element or step not specified and "consisting essentially of"

permits the inclusion of additional unrecited elements or steps that do not materially affect the essential or basic and novel characteristics of the composition or method under consideration.

When concentrations of components in a composition are provided in the form of percentages, it is to be understood that the total of the concentrations in the composition will not exceed 100%.

Emulsifier Composition

As used herein, the terms 'emulsifier composition' or 'emulsifier system' refer to a mixture or combination of ingredients that can stabilize an emulsion or improve the stability of the emulsion. Emulsion stability can be defined as the emulsion's ability to resist changes in its physicochemical properties over time. An emulsion is usually considered stable if it is resistant to physical changes over a practical length of time. The stability of an emulsion can be tested by several methods including centrifugation, filtration, shaking or stirring, low intensity ultrasonic vibration, heating, or simply by observing it as it sits over a period of time. Instability in an emulsion leads to the floating of droplets of the dispersed phase to the surface, creaming precipitation, cohesion between droplets, coalescence of the droplets, and, finally, to separation of the phases. An energy barrier needs to be created at the oil-water interface in an emulsion in order to prevent droplet coalescence (droplet fusion) and to attain reasonable stability of the droplets. An emulsifier provides this energy barrier by forming a stabilizing layer, of, for example, polymers or solid particles, that adsorbs at the oil-water interface. The emulsifier reduces the interfacial tension, preventing emulsion droplets from aggregation or coalescence.

The emulsifier composition of the invention comprises:

a) microcrystalline cellulose;

b) at least one biogum of microbial origin; and, optionally, c) at least one cellulose ether or derivative thereof.

Typically, the microcrystalline cellulose is present in an amount of from about 20 to about 90 wt % based on the total weight of the composition. Typically, the at least one biogum of microbial origin is present in the composition in an amount of from about 10 to about 80 wt % based on the total weight of the composition. "At least one" means "one or more than one". Therefore, the emulsifier composition comprises one biogum of microbial origin or more than one biogum of microbial origin. Typically, the at least one cellulose ether or derivative thereof, when present, is present in an amount of up to about 20 wt % based on the total weight of the composition. Thus, the emulsifier composition can comprise up to about 20 wt % of one or more than one cellulose ether or derivative thereof.

The emulsifier composition of the invention is not surface active and thus it has no tendency to have adverse effects on the skin, such as irritation. It follows that emulsions produced using the emulsifier composition of the invention also can have no tendency to have adverse effects on the skin, such as skin irritation. Further, emulsions produced using the emulsifier composition of the invention: have excellent or improved sensory and rheology properties; have a quick-break effect (i.e., can be easily spread on the skin, leaving no residues); do not require very small droplet sizes, which are commonly required to obtain a stable emulsion, and thus high energy emulsifying methods are not required for producing the emulsions. This last advantage means that processes for producing emulsions using the emulsifier composition of the invention can be relatively technically simple, and thus relatively inexpensive and easy to scale up. It is also of particular note, that the emulsifier composition of the invention contains natural ingredients and thus is environment-friendly, and received better by consumers.

The emulsifier composition of the invention can comprise:

a) from about 20 to about 90 wt % of microcrystalline cellulose;

b) from about 10 to about 80 wt % of at least one biogum produced by microbial fermentation;

wherein by wt % is meant wt % based on the total weight of the emulsifier composition.

Also, the emulsifier composition of the invention can comprise:

a) from about 20 to about 90 wt % of microcrystalline cellulose;

b) from about 10 to about 80 wt % of at least one biogum produced by microbial fermentation; and c) at least one cellulose ether or derivative thereof, wherein the at least one cellulose ether or derivative thereof is present in an amount of up to about 20 wt %, wherein by wt % is meant wt % based on the total weight of the emulsifier composition.

Component a)

The emulsifier composition comprises microcrystalline cellulose (MCC). MCC is purified, partially depolymerized cellulose. Naturally occurring cellulose contains both crystalline and amorphous regions. In contrast, MCC corresponds to isolated crystalline portions of cellulose without the amorphous regions. Isolation of MCC from naturally occurring cellulose typically involves removing amorphous regions of a purified cellulose material by hydrolytic degradation using a strong acid. Typically, MCC is in the form of particulate aggregates, sometimes called "crystallites", having an average particle size in a range of 1 to 400 microns and, more commonly, an average particle size in a range of 10 to 250 microns. The MCC used in the invention can have an average particle size of from 10 to 250 microns or 10 to 200 microns as measured by laser diffraction.

Advantageously, the MCC is present in an amount of from about 30 to about 75%, or from about 40 to about 70% by weight, based on the total amount of the composition.

Component b)

The emulsifier composition comprises at least one biogum of microbial origin. By biogum of microbial origin is meant a biogum which is or can be produced by microbial fermentation. As used herein, a biogum of microbial origin is a polymer, such as a polysaccharide, obtained or obtainable by fermentation of a microorganism. In this context, the term "polymer" can be interchanged with the term "biopolymer". In particular, a biogum of microbial origin is a polymer, such as a polysaccharide, obtained or obtainable by fermentation of a carbohydrate by a microorganism. The microorganism can be chosen from bacteria or fungi. The fermentation can be aerobic fermentation.

The at least one biogum of microbial origin can be chosen from xanthan gum, pullulan gum, sphingan exopolysaccharides, and mixtures thereof. Thus the at least one biogum of microbial origin can be a biogum chosen from xanthan gum, pullulan gum and sphingan exopolysaccharides, or it can be a mixture of biogums chosen from xanthan gum, pullulan gum and sphingan exopolysaccharides.

Xanthan gum is a biogum which can be produced by fermentation of bacteria of the genus *Xanthomonas*, for example, bacteria of the species *Xanthomonas campestris*. More specifically, xanthan gum is a polysaccharide which can be produced, i.e., is obtainable, by fermentation of a carbohydrate by bacteria of the genus *Xanthomonas*, for example, bacteria of the species *Xanthomonas campestris*.

In particular, the xanthan gum is produced by fermentation of a carbohydrate by bacteria of the species *Xanthomonas campestris*. Xanthan gum is a water-soluble, high-molecular weight (of the order of 1000 kDa) polysaccharide. Xanthan gum comprises (or primarily consists of) the following hexose units: D-glucose, D-mannose, and D-glucuronic acid.

Pullulan gum is a biogum which can be produced by fermentation of the fungus *Aureobasidium pullulans*. More specifically, pullulan is a polysaccharide which can be produced, i.e., is obtainable, by fermentation of a carbohydrate, in particular starch, by the fungus *Aureobasidium pullulans*. Pullulan is a polysaccharide consisting of maltotriose units (three glucose units connected by α-1,4 glycosidic bonds) connected to each other by an α-1,6 glycosidic bond.

The terms "sphingan exopolysaccharide" and "sphingan" are used interchangeably herein. Sphingans are biogums which can be produced by bacteria of the genus *Sphingomonas*. Sphingans are structurally closely related bacterial exopolysaccharides produced by members of the genus *Sphingomonas*. Sphingan exopolysaccharides can be produced, i.e., are obtainable, by fermentation of a carbohydrate by bacteria of the genus *Sphingomonas*. The most commonly known sphingans include gellan, welan, rhamsan and diutan and these exhibit excellent rheological properties. Sphingans are structurally related by a backbone that comprises the sugars D-glucose, D-glucuronic acid and L-rhamnose (or L-mannose) but differ in the nature and location of their side-chains and in the presence or absence of acyl groups. Details of the structures of sphingans can be found in the literature, for instance in a book by Glaeser S. P., Kampfer P. (2014) The Family Sphingomonadaceae, and in Rosenberg E., DeLong E. F., Lory S., Stackebrandt E., Thompson F. (eds), The Prokaryotes, Springer, Berlin, Heidelberg. The at least one biogum of microbial origin can be chosen from the group of sphingan exopolysaccharides consisting of gellan, welan, diutan gum and mixtures thereof. Thus the at least one biogum of microbial origin can be a biogum chosen from gellan, welan and diutan gum, or it can be a mixture of biogums chosen from gellan, welan and diutan gum.

Welan gum is a biogum which can be produced by fermentation of bacteria from the genus *Alcaligenes* or the genus *Sphingomonas*. More specifically, welan gum is an exopolysaccharide that can be produced, i.e., is obtainable, by fermentation of a carbohydrate by bacteria from the genus *Alcaligenes* or the genus *Sphingomonas*. Welan gum is a polymer that has a repeating tetrasaccharide backbone chain containing L-mannose, L-rhamnose, D-glucose, and D-glucuronic acid. In one particular embodiment, the welan gum is obtained by fermentation of a carbohydrate by bacteria from genus *Sphingomonas*.

Gellan gum is a biogum which can be produced by fermentation of bacteria of the species *Sphingomonas elodea*. Gellan gum is a water-soluble anionic polysaccharide produced by the bacterium *Sphingomonas elodea*. More specifically, gellan gum is an exopolysaccharide that can be produced, i.e., is obtainable, by fermentation of a carbohydrate by bacteria of the species *Sphingomonas elodea*. It is a polymer which has, as a repeating unit, a tetrasaccharide which consists of two residues of D-glucose and one each of a residue of L-rhamnose and D-glucuronic acid.

Diutan gum, also known as heteropolysaccharide S-657, is a biogum which is produced by fermentation of a bacteria strain from genus *Sphingomonas*, for example, a bacteria strain from genus *Sphingomonas* deposited in the American Type Culture Collection (ATCC) with deposit number ATCC 53159. More specifically, diutan gum is an exopolysaccharide that can be produced, i.e., is obtainable, by fermentation of a carbohydrate by bacteria from the genus *Sphingomonas*, and, in particular, a bacteria strain from genus *Sphingomonas* having a deposit number ATCC 53159. Diutan generally exhibits a hexameric repeat unit consisting of four sugars in the backbone (glucose-glucuronic acid-glucose-rhamnose) and a side chain of two rhamnose residues attached to one of the glucose residues. One non-limiting example of commercially available diutan gum is Kelcocare™ diutan gum from CP Kelco. Diutan gum is also commonly referred as S-657 polysaccharide.

Advantageously, the at least one biogum of microbial origin can be present from about 20 to about 75 wt %, or from about 25 to about 45 wt %, or from about 25 to about 35 wt %, based on the total weight of the composition.

Surprisingly, it has been found that diutan gum provides a synergistic emulsifier effect when combined with MCC and, particularly, when combined with MCC and at least one cellulose ether. Thus, in one embodiment, the at least one biogum of microbial origin is or comprises diutan gum.

Component c)

The emulsifier composition can optionally comprise at least one cellulose ether or derivative thereof.

Cellulose ethers are cellulose derivatives in which hydrogen atoms of hydroxyl groups of glucopyranose monomers that make up the cellulose backbone are replaced, for example, with alkyl groups, hydroxyalkyl groups or carboxyalkyl groups. The degree of substitution of the hydrogen atoms varies. The cellulose ethers and derivatives thereof used in the invention are water dispersible. Examples of cellulose ethers include alkyl celluloses, hydroxyalkylcelluloses and carboxyalkylcelluloses. Typically, each alkyl group is, independently, a C1 to C4, C1 to C3, C1 to C2, or C1 alkyl group. Examples of derivatives of cellulose ethers include salts of carboxyalkylcellulose, such as sodium salt. Thus the at least one cellulose ether or derivative thereof can be a cellulose ether or derivative thereof chosen from alkyl celluloses, hydroxyalkylcelluloses, carboxyalkylcelluloses and sodium salts of carboxyalkylcelluloses, the at least one cellulose ether or derivative thereof can be a mixture of cellulose ethers or derivatives thereof chosen from alkyl celluloses, hydroxyalkylcelluloses, carboxyalkylcelluloses and sodium salts of carboxyalkylcelluloses. Preferably, each alkyl group is, independently, C1 to C3, or C1 to C2, or C1 alkyl group. Non-limiting examples of suitable cellulose ethers and derivatives thereof include methyl cellulose, ethyl cellulose, hydroxyethyl cellulose, hydroxyethylmethylcellulose, methylhydroxyethylcellulose, hydroxypropylcellulose (HPC), hydroxypropylmethylcellulose (HPMC), carboxymethylcellulose (CMC), sodium carboxymethylcellulose (NaCMC) and mixtures thereof. NaCMC is also commonly referred as cellulose gum. NaCMC is a cellulose derivative with carboxymethyl groups bound to some of the hydroxyl groups of the glucopyranose monomers that make up the cellulose backbone.

Advantageously, when present, the at least one cellulose ether or derivative thereof can be present from about 5 to about 20 wt %, about 5 to about 15 wt %, or from about 8 to about 12 wt %, based on the total weight of the composition.

It has been found that the presence of sodium carboxymethyl cellulose (NaCMC) in the emulsifier composition of the invention improves significantly the stability of the emulsion and the sensorial properties (such as improved spreadability, reduced tackiness, no residue left on the skin and it does not alter the properties of the oil) of personal care formulations.

The emulsifier composition of the invention can comprise a) from about 30 to about 75 wt % or from about 40 to about 70 wt % of microcrystalline cellulose;

b) from about 20 to about 75 wt % of at least one biogum produced by microbial fermentation; and, optionally, c) from about 5 to about 15 wt % of at least one cellulose ether or derivative thereof, wherein by wt % is meant wt % based on the total weight of the emulsifier composition.

The emulsifier composition of the invention can comprise:

a) from about 30 to about 75 wt % or from about 40 to about 70 wt % of microcrystalline cellulose;

b) from about 20 to about 75 wt % of at least one biogum produced by microbial fermentation; and, optionally, c) from about 8 to about 12 wt % of at least one cellulose ether or derivative thereof, wherein by wt % is meant wt % based on the total weight of the emulsifier composition.

The emulsifier composition of the invention can comprise:

a) from about 30 to about 75 wt % or from about 40 to about 70 wt % of microcrystalline cellulose;

b) from about 25 to about 45 wt % of at least one biogum produced by microbial fermentation; and, optionally, c) from about 5 to about 15 wt % of at least one cellulose ether or derivative thereof, where by wt % is meant wt % based on the total weight of the emulsifier composition.

The emulsifier composition of the invention can comprise:

a) from about 30 to about 75 wt % or from about 40 to about 70 wt % of microcrystalline cellulose;

b) from about 25 to about 45 wt % of at least one biogum produced by microbial fermentation; and, optionally, c) from about 8 to about 12 wt % of at least one cellulose ether or derivative thereof, where by wt % is meant wt % based on the total weight of the emulsifier composition.

The emulsifier composition of the invention can comprise:

a) from about 30 to about 75 wt % or from about 40 to about 70 wt % of microcrystalline cellulose;

b) from about 25 to about 35 wt % of at least one biogum produced by microbial fermentation; and, optionally, c) from about 5 to about 15 wt % of at least one cellulose ether or derivative thereof, where by wt % is meant wt % based on the total weight of the emulsifier composition.

The emulsifier composition of the invention can comprise:

a) from about 30 to about 75 wt % or from about 40 to about 70 wt % of microcrystalline cellulose;

b) from about 25 to about 35 wt % of at least one biogum produced by microbial fermentation; and, optionally, c) from about 8 to about 12 wt % of at least one cellulose ether or derivative thereof, where by wt % is meant wt % based on the total weight of the emulsifier composition.

The ratios of components a) and b) and c) (when c) is present) may advantageously influence the properties of the composition.

The weight ratio of MCC:biogum of microbial origin can be from 1:2 to 4:1. In particular, the concentration of MCC can be higher than the biogum of microbial origin, where concentration is wt % based on the total weight of the emulsifier composition. For example, the weight ratio of a):b) can be from 2:1 to 4:1.

The weight ratio of MCC:cellulose ether or derivative thereof can be from 10-2:1, particularly from 9-3:1, more particularly from 5-3:1.

The weight ratio of MCC:biogum of microbial origin: cellulose ether or derivative thereof is from 2 to 8 of MCC, from 1 to 20 of biogum, and the cellulose ether is 1, i.e., 2-8:1-20:1. Advantageously, the ratio is from 3 to 6 of MCC, from 1 to 10 of biogum and the cellulose ether is 1 (3-6:1-10:1); or from 4 to 5.5 of MCC, from 1 to 3.5 of biogum and the cellulose ether is 1 (4-5.5:1-3:1) or from 4.5 to 5.5 of MCC, from 1.5 to 3 of biogum and the cellulose ether is 1 (4-5.5:1.5-3:1).

Exemplary embodiments of the emulsifier composition of the invention include:

I An emulsifier composition comprising:

a) from about 40 to about 70 wt % of microcrystalline cellulose;

b) from about 25 to about 35 wt % of at least one biogum produced by microbial fermentation, wherein said at least one biogum is or comprises diutan; and c) from about 8 to about 12 wt % of at least one cellulose ether or derivative thereof, wherein by wt % is meant wt % based on the total weight of the emulsifier composition and wherein the weight ratio of a):b):c) is 2-8:1-20:1 or 3-6:1-10:1.

II An emulsifier composition comprising:

a) from about 40 to about 70 wt % of microcrystalline cellulose;

b) from about 25 to about 35 wt % of at least one biogum produced by microbial fermentation, wherein said at least one biogum is or comprises diutan; and, c) from about 8 to about 12 wt % of at least one cellulose ether or derivative thereof, wherein said at least one cellulose ether or derivative thereof is or comprises sodium carboxymethylcellulose, wherein by wt % is meant wt % based on the total weight of the emulsifier composition and wherein the weight ratio of a):b):c) is 2-8:1-20:1 or 3-6:1-10:1.

Other components can be present in the emulsifier composition and these include, co-emulsifiers, thickening agents, dispersants, fragrances or other additives with a scenting function, pigments, preservatives and combinations thereof. These can be present in an amount of up to 20 or 10 wt % of the emulsifier composition, i.e., the emulsifier composition comprises at least 80 or 90 wt % of components a) and b), when c) is not present, and the emulsifier composition comprises at least 80 or 90 wt % of components a), b) and c), when c) is present.

Preferably, the emulsifier composition of the invention is anhydrous. The term 'anhydrous' as used herein means that that the emulsifier composition comprises up to 10% by weight water. Particularly, the emulsifier composition comprises up to 7% by weight water, and, more particularly, it comprises up to 5% or up to 2% by weight water, based on the total weight of the composition. The emulsifier compositions can contain only the residual amounts of water from the raw materials used. The emulsifier composition can consist essentially of components a), b) and c), with, for example, any impurities present being due to raw materials used.

The emulsifier composition of the invention is not surface active, where being surface active is defined in Example 3.

Personal Care Formulations

The emulsifier composition of the invention is suitable for use in forming and stabilizing emulsions which can be used in personal care formulations. The invention extends to an emulsion comprising an emulsifier composition as described herein. The emulsion can comprise: i) a water phase; ii) an oil phase, and iii) an emulsifier composition as described herein. The invention extends to a personal care formulation comprising an emulsifier composition as described herein. The personal care formulation can comprise: i) a water phase; ii) an oil phase, and iii) an emulsifier composition as described herein.

The term "personal care" as used herein when applied to formulations/products includes but is not limited to cosmetics, toiletries, cosmeceuticals, beauty aids, insect repellents, personal hygiene and cleansing products applied to the body, including the skin, hair, scalp, and nails of humans and animals.

The emulsion or the personal care formulation of the invention comprises an oil phase. As used herein, the term "oil" means a compound or a mixture of compounds that is insoluble in water and has a liquid appearance at a temperature of 25° C. The oil phase is not restricted to a specific oil. Any oil suitable for cosmetic or personal care formulations can be used, including but not limited to, vegetable oils, oils derived from petroleum (e.g., mineral oils, liquid paraffin), fatty esters, etc.

The oil phase may comprise at least one of an ester oil, vegetable oil, alcohol, paraffin oil or silicone. The oil phase can comprise one or more oils chosen from mineral oils such as paraffin oil, petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheat germ oil, corn germ oil, soybean oil, cottonseed oil, alfalfa oil, poppy oil, pumpkin oil, evening primrose oil, millet oil, barley oil, rye oil, safflower oil, bancoulier oil, passionflower oil, hazelnut oil, palm oil, shea butter, apricot kernel oil, coriander seed oil, beech oil, calophyllum oil, sysymbrium oil, avocado oil, calendula oil, oils from flowers or vegetables ethoxylated vegetable oils; synthetic oils such as fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, esters derived from linoleic acid, such as isopropyl lanolate, isocetyl lanolate, monoglycerides, diglycerides and triglycerides of fatty acids such as glycerol triheptanoate, alkylbenzoates, hydrogenated oils, poly (alpha-olefins), polyolefins such as poly (isobutane), synthetic isoalkanes such as isohexadecane, isododecane, perfluorinated oils; silicone oils such as dimethylpolysiloxanes, methylphenylpolysiloxanes, amino-modified silicones, fatty acid-modified silicones, alcohol-modified silicones, alcohol-modified silicones and fatty acids, silicone-modified silicones polyether groups, modified epoxy silicones, silicones modified by fluorinated groups, cyclic silicones and silicones modified by alkyl groups.

The oil phase can contain, e.g., other components that are oil soluble. The oil phase can comprise at least 90 wt %, at least 95 wt %, or at least 98 wt %, of one or more than one oils, based on the total weight of the oil phase.

The emulsion or the personal care formulation of the invention comprises a water phase. The water phase comprises water and can contain, e.g., other components that are water soluble. The water phase can comprise at least 90 wt %, at least 95 wt %, or at least 98 wt % water, based on the total weight of the water phase.

The emulsion or the personal care formulation can be an oil-in-water (O/W) emulsion, a water-in-oil emulsion (W/O), or an oil in polyol (e.g., glycerol) emulsion. The emulsion or the personal care formulation can also be a multiple emulsion, in which O/W and W/O emulsions exist in a single system. In a multiple emulsion, the dispersed phase is itself an emulsion containing droplets of another phase. The dispersed phase can be a multiple emulsion such as a water-in-oil-in-water emulsion (W/O/W) or an oil-in-water-in-oil emulsion (O/W/O).

The emulsion or the personal care formulation can be a W/O emulsion, i.e., where the oil phase is the continuous phase and the water phase is the dispersed phase. Typically, in this embodiment, the oil phase will have a larger volume than the volume of the water phase.

In particular, the emulsion or the personal care formulation can be an O/W emulsion, with the water phase forming the continuous phase and the oil phase forming the dispersed phase. The emulsifier composition of the invention exhibits a surprisingly improved performance in O/W emulsions compared to other emulsifier compositions or systems. For example, the emulsifier composition of the invention enables a higher concentration of oil to be present in the O/W emulsion, can be used to produce emulsions that are more stable compared to those obtained using other emulsifier systems, and is effective when present in relatively low concentrations.

When the emulsion or the personal care formulation is an O/W emulsion, the oil phase may be present in an amount of from 1 to 50% by weight based on the total weight of the emulsion or the personal care formulation. As mentioned, one of the advantages of the emulsifier composition of the invention is that it can facilitate the provision of emulsions with a high oil content. Thus, the oil phase may be present in an amount of greater than or equal to 5%, particularly greater than or equal to 20%, 30% or 40% by weight based on the total weight of the emulsion or the personal care formulation. The oil phase may be present from 5 to 40%, particularly 10 to 30%, more particularly from 20 to 30% by weight based on the total weight of the emulsion or the personal care formulation.

Preferably, the emulsion or the personal care formulation of the invention comprises at least 0.1% by weight of the emulsifier composition of the invention, based on the total weight of the emulsion or the personal care formulation. The emulsifier composition can be present in the emulsion or the personal care formulation in an amount of from 0.1 to 5% by weight, particularly from 0.2 to 1.5% by weight, more particularly from 0.5 to 1% by weight based on the total weight of the emulsion or the personal care formulation. The amount of emulsifier composition present in the emulsion or the personal care formulation can be 0.6, 0.7, 0.8 and 0.9% by weight based on the total weight of the emulsion or the personal care formulation. In one embodiment, the emulsifier composition is present in the emulsion or the personal care formulation in an amount of 0.7% by weight based on the total weight of the emulsion or personal care formulation.

Thus, the invention provides an emulsion or a personal care formulation comprising:

i) a water phase;

ii) an oil phase; and iii) at least 0.1 wt % of the emulsifier composition of the invention, where wt % is based on the total weight of the emulsion or the personal care formulation.

The amount of MCC present in the emulsion or the emulsion or the personal care formulation may range from 0.05 to 5.0% by weight based on the total weight of the emulsion or the personal care formulation. Advantageously, MCC is present from 0.1 to 2.5%, particularly from 0.1 to 1.0%, particularly from 0.1-0.49%, more particularly from 0.35-0.45% by weight, based on the total weight of the emulsion or the personal care formulation. The MCC concentration can be 0.45, 0.42, 0.40, 0.38, 0.35% by weight based on the total weight of the emulsion or the personal care formulation.

The amount of biogum of microbial origin present in the emulsion or the personal care formulation may range from 0.02 to 2.5% by weight based on the weight of the emulsion or the formulation. Advantageously, the biogum if microbial origin is present from 0.05 to 1.5%, particularly from 0.05 to 0.5%, more particularly is in the range from 0.1 to 0.3% by weight based on the total weight of the emulsion or the formulation. The biogum of microbial origin can be present in the personal care formulation in an amount of 0.25, 0.2, 0.15% by weight based on the total weight of the emulsion or the formulation.

The amount of cellulose ether or derivative thereof present in the emulsion or the personal care formulation may range from 0 to 1% by weight based on the total weight of the emulsion or the formulation. Advantageously, the amount of cellulose ether may be from 0.01 to 0.5%, particularly from 0.05 to 0.2% or 0.06 to 0.1% by weight based on the total weight of the emulsion or the formulation. The cellulose ether or derivative thereof can be present in the emulsion or the personal care formulation in an amount of 0.02, 0.04, 0.05, 0.06, 0.08, 0.12 or 0.14% by weight based on the total weight of the emulsion or the formulation.

Thus, the invention provides an emulsion or a personal care formulation comprising:

i) a water phase;

ii) an oil phase, iii) 0.05 to 5.0 wt % of MCC;

iv) 0.02 to 2.5 wt % of at least one biogum of microbial origin; and v) 0 to 1 wt % of at least one cellulose ether or derivative thereof, wherein wt % is based on the total weight of the emulsion or the personal care formulation.

The emulsions and personal care formulations of the invention may be made by generally conventional emulsification and mixing methods known to the skilled person. One of the advantages of the emulsifier composition according to the invention is that, when used to form emulsions, the size of the droplets of the dispersed phase is not required to be very small and thus high energy emulsifying methods are not necessary in the preparation of the emulsions. This leads to a formulation process that is technically simpler, cheaper and easier to scale up.

The invention provides a method of preparing an emulsion or a personal care formulation comprising an oil phase and a water phase, where the method comprises the step of mixing the emulsifier composition of the invention with the oil phase and the water phase. Preferably, the emulsifier composition is first mixed with the water phase and then the oil phase is mixed with the mixture of the water phase and the emulsifier composition. The emulsion or the personal care formulation can be as described herein.

The method of preparing an emulsion or a personal care formulation may comprise the steps of:

i) dispersing the emulsifier composition of the invention into a water phase;

ii) stirring the oil phase into the water phase to form an emulsion; and, optionally, iii) adjusting the pH of the emulsion to lower than 7.

The stirring conditions of step ii) are preferably slow stirring conditions and may comprise stirring at stirring speeds of from 5000 to 20000 rpm, particularly from 8000-12000 rpm. In one embodiment, the stirring speed is lower than 12000 rpm. The emulsion or the personal care formulation can be as described herein.

In step iii) the pH is preferably adjusting by using an acid, preferably a weak acid such as citric acid. In step iii), the pH can be adjusted to 5.5.

The invention provides a method of stabilizing an emulsion comprising an oil phase and a water phase, comprising a step of mixing the emulsifier composition of the invention with the oil phase and the water phase. Preferably, the emulsifier composition is first mixed with the water phase and then the oil phase is mixed with the mixture of the water phase and the emulsifier composition. The emulsion can be as described herein or can be a personal care formulation as described herein.

The invention provides for the use of the emulsifier composition of the invention to stabilize an emulsion comprising an oil phase and a water phase. The emulsion can be an emulsion as described herein or a personal care formulation as described herein.

The personal care formulation may be in the form of a lotion, cream or gel cream, or any forms of emulsion known in the art.

The personal care formulation is preferably a skin care product for example a sunscreen, cosmetic, antiperspirant, depilatory or dermatological product, or a hair care product for example a shampoo, conditioner, hair dye or hair relaxer product.

The personal care formulation can also be included in fabrics, non-woven fabrics, garments, medical devices and means for immobilizing the compounds to them. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The personal care formulation of the invention can contain other components such as co-emulsifiers and rheology modifiers. Preferably the other components are present in an amount of less than 10 wt %, particularly less than 5 wt %, more particularly less than 1 wt % of the personal care formulation. In addition, or alternatively, the water phase, oil phase and emulsifier composition combined are present in an amount of greater than 90 wt %, particularly greater than 95 wt %, more particularly greater than 99 wt % of the personal care formulation.

Co-Emulsifiers

The addition of further co-emulsifiers to the personal care formulation can be of advantage. The term 'co-emulsifiers' is well known in the art. It refers to compounds that, generally, are combined with emulsifiers in order to improve the viscosity and stability of the resulting emulsion.

The concentration of co-emulsifier may range between 0.1 and 2%, particularly from 0.2 to 1% by weight, more particularly from 0.4 to 0.6% by weight based on the final weight of the formulation. One of the advantages of the emulsifier compositions of the present invention is that, when used to form an emulsion, the concentration of co-emulsifier can be lower than is required for other emulsion systems. This avoids problems of irritation to the skin if surfactants are used as the co-emulsifier, or loss of sensory parameters and consumer acceptance. Therefore, preferably, the concentration of co-emulsifier is lower than 0.6% by weight based on the total weight of the formulation.

Co-emulsifiers of natural origin are particularly advantageous in the context of the present invention. Examples of natural co-emulsifiers include, but are not limited to, fatty alcohols, glyceryl caprylate, polyglyceryl-3 laurate, glyceryl stearate, glyceryl stearate citrate, cetearyl olivate, sorbitan olivate, potassium cetyl phosphate, sodium or potassium stearate, sucrates, sucrose esters of fatty acids, lactates, and mixtures thereof.

The term 'fatty alcohol' as used herein refers to long-chain primary alcohols, preferably with a chain length of 16 to 26 carbon atoms, which may be derived from natural sources such as fats and oils. Examples of fatty alcohols suitable for the present invention include but are not limited to the group selected from the group comprising cetyl alcohol, cetostearyl alcohol, palmitoleyl alcohol, stearyl alcohol, isostearyl alcohol, oleyl alcohol, arachidyl alcohol, behenyl alcohol, isobehenyl alcohol, erucyl alcohol, lignoceryl alcohol and cerotinyl alcohol. Particularly, fatty alcohols used in the present invention are selected from cetyl alcohol, cetostearyl alcohol (or cetearyl alcohol), stearyl alcohol, isostearyl alcohol, arachidyl alcohol, behenyl alcohol, isobehenyl alcohol, lignoceryl alcohol and cerotinyl alcohol. More particularly, the fatty alcohol is cetostearyl alcohol.

The personal care formulation may also include alkoxylated fatty alcohols as co-emulsifiers. Alkoxylated fatty alcohols are known in the art. As such, their production would be well known to the skilled person.

Particularly, glyceryl caprylate and polyglyceryl-3 laurate significantly improve the stability of the emulsion in combination with the emulsifier composition of the invention. Thus, in one embodiment the co-emulsifier is selected from the group of glyceryl caprylate and polyglyceryl-3 laurate, and mixtures thereof. More particularly, the co-emulsifier is polyglyceryl-3 laurate.

Rheology Modifiers

The personal care formulation may further comprise rheology modifiers such as thickening and/or gelling agents to improve the rheology of the formulation depending on the product specification.

Non-limiting examples include polymers of polyelectrolyte type, linear or branched or crosslinked, such as the homopolymer of partially or fully salified acrylic acid, the homopolymer of partially or fully salified methacrylic acid, the homopolymer of 2-acrylamido-2-methyl-[(1-oxo-2-propenyl) amino]-1-propanesulfonic acid (AMPS) partially or totally salified, copolymers of acrylic acid and AMPS, copolymers of acrylamide and AMPS, copolymers of vinyl pyrrolidone and AMPS, copolymers of AMPS and (2-hydroxyethyl) acrylate, copolymers of AMPS and (2-hydroxyethyl methacrylate), copolymers of AMPS and hydroxyethyl acrylamide, copolymers of AMPS and N,N-dimethyl acrylamide, the copolymers of AMPS and tris (hydroxy-methyl) acrylamidomethane (THAM), copolymers of acrylic or methacrylic acid and (2-hydroxy ethyl acrylate), copolymers of acrylic or methacrylic acid and (2-hydroxy ethyl methacrylate), copolymers of acrylic or methacrylic acid and hydroxyethyl acrylamide, copolymers of acrylic or methacrylic acid and THAM, copolymers of acrylic or methacrylic acid and N,N-dimethyl acrylamide, terpolymers of acrylic acid or methacrylic acid, AMPS and (2-hydroxyethyl acrylate), terpolymers of acrylic or methacrylic acid, AMPS and (2-hydroxy ethyl methacrylate), terpolymers of acrylic or methacrylic acid, AMPS and THAM, terpolymers of acrylic or methacrylic acid, AMPS and N,N-dimethyl acrylamide, terpolymers of acrylic or methacrylic acid, AMPS and acrylamide, copolymers of acrylic acid or methacrylic acid and alkyl acrylates.

In one embodiment, the thickener and/or gelling agent of the invention is of natural origin.

Natural gums are of particular interest. Natural gums are non-cellulose polysaccharides derived from botanical sources, seaweeds, or produced via bacterial fermentation. Non-limiting examples of plant-derived natural gums include *albizia* gum, aloe mucilage, beta-glucan, *cassia* gum, chicle gum, dammar gum, fenugreek gum, glucomannan, guar gum, gum arabic (also called acacia gum), gum copal, gum ghatti, gum tragacanth, hakea gum, *Hibiscus rosa sinensis* gum, honey locust gum, hupu gum, karaya gum, khaya gum, *Lepidium sativum* gum, locust bean gum, mastic gum, *Mimosa scabrella* gum, *Mimosa pudica* gum, okra gum, *psyllium* seed husks (also called ispaghula husk), spruce gum, *Sterculia foetida* gum, tamarind gum, tara gum, and derivatives of any of the foregoing. Examples of natural gums derived from seaweeds include, without limit, alginate or alginic acid, fucoidan, and laminarin derived from brown seaweeds, and agar and carrageenans derived from red seaweeds. In one particular embodiment, the natural gum is selected from the group of tara gum or *cassia* gum.

The inventors have found that the addition of starch derivatives can be particularly useful for increasing the viscosity of the emulsion system so as to obtain gel cream emulsions that can be of interest in certain cosmetic applications. Without addition of starch derivatives, fluid emulsion lotions can be obtained. Non-limiting example of starch derivatives include starch oxide, dialdehyde starch, dextrin, British gum, acetyl starch, starch phosphate, carboxymethyl starch, hydroxyethyl starch, hydroxypropyl starch. Starch derivatives show a synergistic effect when combined with the MCC, the at least one biogum of microbial origin and the at least on cellulose ether or derivative thereof of the emulsifying composition of the invention, compared to other emulsifier compositions.

The starch derivative may be present in the personal care formulation in an amount of from 0.1 and 2% by weight, and particularly from 0.2 to 1% by weight, based on the total weight of the formulation. More particularly, the derivative starch derivative is present in the personal care formulation in an amount of 0.3, 0.4, 0.5, 0.6 or 0.7% by weight, based on the total weight of the formulation.

The personal care formulation of the invention can have a viscosity of from 1000 to 4000 mPa·s, particularly from 2000 to 3000 mPa·s, more particularly from 2500 to 2000 mPa·S when determined in mPa·s at 25° C. with a Brookfield LVT viscometer using an appropriate spindle depending on the viscosity of the emulsion, tested at 20 rpm, and where viscosity is determined at 24 h after the emulsion was prepared.

The personal care formulation of the invention can comprise at least one co-emulsifier and at least one starch derivative.

Other Optional Ingredients

The personal care formulation may contain many different ingredients that can be oil soluble, water soluble or non-soluble. Non-limiting examples of said ingredients include, preservatives, perfumes, humectants or solvents such as alcohols, polyols such as glycerol and polyethylene glycols, sun filters or sunscreen ingredients, alpha hydroxyacids, antimicrobial, vitamins and their precursors (such as Vitamin A, B, C, D, F and precursors thereof), skin care active ingredients or agents, botanical extracts, insect repellents, essential oils, pigments (such as y oxides and silicates, iron oxide, particularly coated iron oxides, and/or titanium dioxide, and ceramic materials such as boron nitride), deodorant or antiperspirant agents, depilatory agents, hair care agents (such as condition agents, hair dyes, hair relaxer, etc.), and combinations thereof.

The personal care formulation may include preservatives common in personal care such as for example, but not limited to phenoxyethanol, formaldehyde solution, pentanediol or sorbic acid.

The personal care composition may be combined with antioxidant agents. Non-limiting examples include EDTA and its salts, citric acid, tartaric acid, oxalic acid, BHA (butylhydroxyanisol), BHT (butylhydroxytoluene), tocopherol derivatives such as tocopherol acetate, and mixtures thereof.

The personal care composition may further include personal care active ingredients or pharmaceutically active agents. In the context of this invention, the 'personal care active ingredients' as used herein refers to ingredients that improve or enhance the physical appearance. They are also commonly known as 'cosmetic active ingredients'.

Among the cosmetically or pharmaceutically acceptable ingredients contained in the personal care formulations described in this invention are ingredients commonly used in cosmetic or pharmaceutical compositions, for example and, not restricted to, (i) anti-wrinkle agents, Botox®-like agents and/or anti-aging agents; (ii) firming agents, skin elasticity agents and/or restructuring agents; (iii) moisturizing agents; (iv) anti-photoaging agents, and/or blue-light protector agents; DNA protecting agents, DNA repair agents, and/or stem cell protecting agents; (v) free radical scavengers and/or anti-glycation agents, detoxifying agents, antioxidant and/or anti-pollution agents; (v) agents which increase the percutaneous absorption of any active compounds present therein; (vi) anti-perspirant agents; (vii) melanin synthesis stimulating or inhibiting agents; whitening or depigmenting agents; propigmenting agents; self-tanning agents; (viii) lipolytic agents or agents stimulating lipolysis, adipogenic agents, etc.

In one embodiment, the personal care formulation is a cosmetic or pharmaceutical composition comprising a pharmaceutically or cosmetically effective amount of an adjuvant selected from the group consisting of: (i) anti-wrinkle-agent, Botox-like agent and/or anti-aging agent; (ii) firming agent, skin elasticity agent and/or restructuring agent; (iii) moisturizing agent; (iv) anti-photoaging agent, and/or blue-light protector agent; (v) DNA protecting agent, DNA repair agent, and/or stem cell protecting agent; (vi) free radical scavengers and/or anti-glycation agent, detoxifying agent, antioxidant and/or anti-pollution agents; and/or combinations thereof.

The anti-wrinkle agent, Botox-like agent and/or anti-aging agent can be selected from the group consisting of Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6 [INCI: Glycerin, Water, Hydroxypropyl Cyclodextrin, Palmitoyl Tripeptide-38], Matrixyl® Morphomics™ [INCI: Pentylene Glycol, Caprylyl Glycol], Essenskin™ [INCI: calcium hydroxymethionine], Renovage [INCI: Teprenone], Dermaxyl® [INCI: Palmitoyl Oligopeptide], Calmosensine™ [INCI: Butylene Glycol, Acetyl Dipeptide-1 Cetyl Ester], Volulip™ [INCI: Cetearyl Ethylhexanoate, Sorbitan Isostearate, *Portulaca pilosa* Extract, Sucrose Cocoate, Palmitoyl Tripeptide-38], Subliskin™ [INCI: *Sinorhizobium meliloti* Ferment, Cetyl Hydroxyethyl Cellulose, Lecithin], Biopeptide™ CL [INCI: Palmitoyl Oligopeptide], Biopeptide™ EL [INCI: Palmitoyl Oligopeptide], Rigin™ [INCI: Palmitoyl Tetrapeptide-3], Bio-bustyl™ [INCI: Glyceryl Polymethacrylate, Rahnella/Soy Protein Ferment, Palmitoyl Oligopeptide], Dynalift™ [INCI: Sodium Polystyrene Sulfonate, *Sorghum Bicolor* Stalk Juice, Glycerin], Idealift [INCI: Acetyl Dipeptide-1 Cetyl Ester], Siegesbeckia [INCI: Siegesbeckia Orientales Extract], Ovaliss™ [INCI: Coco-glucoside, Caprylyl Glycol, Alcohol, Glaucine], Juvinity™ [INCI: Geranylgeranyl isopropanol], Prolevis™ [INCI: Hydrolyzed Vegetable Protein], Idealift™ [INCI: Hydroxyethylcellulose, Acetyl Dipeptide-1 cetyl ester], Beautifeye™ [INCI: *Albizia julibrissin* Bark Extract, Darutoside], Chromocare™ [INCI: *Sigesbeckia orientalis* Extract, *Rabdosia rubescens* Extract] or Resistem™ [INCI proposed: *Globularia cordifolia* Ferment] marketed by Sederma/Croda. Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: *Ceratonia siliqua* (Carob) Gum], Preregen® [INCI: *Glycine soja* (Soybean) Protein, Oxido Reductases], Pepha-Nutrix™ [INCI: Natural Nutrition Factors], Pepha-Tight™ [INCI: Algae Extract, Pullulan], Pentacare-NA™ [INCI: Hydrolyzed Wheat Gluten, *Ceratonia siliqua* Gum], Syn®-Tacks [INCI: Glycerin, Palmitoyl Dipeptide-5 Diaminobutyroyl Hydroxythreonine, Palmitoyl Dipeptide-6 Diaminohydroxybutyrate], BeauActive™ MTP [INCI: Hydrolyzed milk protein], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine], Syn®-Hycan [INCI: Tetradecyl Aminobutyroylvalylaminobutyric Urea Trifluoroacetate], Syn®-Glycan [INCI: Tetradecyl Aminobutyroylvalyl-aminobutyric Urea Trifluoroacetate], Regu-Age™ [INCI: Hydrolyzed Rice Bran Protein, Oxido Reductases, *Glycine Soja* Protein], Pepha-Timp™ [INCI: Human oligopeptide-20], Pepha-Age™ [INCI: *Dunaliella Salina* Extract], Colhibin™ [INCI: Hydrolyzed Rice Protein], Elhibin™ [INCI: *Glycine Soja* Protein, Disodium cocoamphodiacetate] or All-Q™ Plus [INCI: Ubiquinone, Tocopheryl Acetate] marketed by Pentapharm/DSM; Myoxinol™ [INCI: Hydrolyzed *Hibiscus esculentus* Extract], Myoxinol™ LS 9736 [INCI: Hydrolyzed *Hibiscus esculentus* Extract, Dextrin], Syniorage™ [INCI: Acetyl Tetrapeptide-11], Dermican™ [INCI: Acetyl Tetrapeptide-9], DN-AGE® LS [INCI: *Cassia alata* leaf Extract], Hyalufix™ GL [INCI: Alpinia Galanga Leaf Extract], Neurobiox™ [INCI: *Achillea millefolium* Extract,], Deliner™ [INCI: *Zea mays* (Corn) Kernel Extract], Lys'lastine V™ [INCI: *Peucedanum graveolens* (Dill) Extract], Extracellium™ [INCI: Hydrolyzed Potato Protein], Proteasyl™ TP LS 8657 [INCI: *Pisum Sativum* Extract], Flavagrum™ PEG [INCI: PEG-6 Isostearate, Hesperetin Laurate], Micromerol™ [INCI: *Pyrus malus* Fruit Extract], Marine Filling Spheres [INCI: Pentaerythrityl Tetraisostearate, Silica Dimethyl Silylate, Sodium Chondroitin Sulfate, Atelocollagen], Triactigen™ [INCI: Mannitol, Cyclodextrin, Yeast Extract, Disodium Succinate], Eterniskin [INCI: Grifola *Frondosa* Fruiting Body Extract, Maltodextrin], Ascotide™ [INCI: Ascorbyl Phosphate Succinoyl Pentapeptide-12], Hyalurosmooth™ [INCI: *Cassia Angustifolia* Seed Polysaccharide], Indinyl™ CA [INCI: *Cassia angustifolia* Seed Polysaccharide], Arganyl [INCI: Argania *Spinosa* Leaf Extract], Sphingoceryl Veg™ [INCI: Phyto-ceramides], Vit-A-Like™ [INCI: *Vigna*

*aconitifolia* Seed Extract], Peptiskin™ [INCI: Arginine/Lysine polypeptide], Prodejine™ [INCI: Mannitol, Cyclodextrin, Yeast Extract, Disodium Succinate], Aqu'activ [INCI: Behenyl Alcohol, Glyceryl Oleate, Cocamide MIPA, Calcium Citrate], Elestan™ [INCI: Glycerin, *Manilkara* Leaf Extract], Hibiscin™ HP [INCI: *Hibiscus esculentus* Seed Extract], Collalift® 18 [INCI: Khaya *Senegalensis* Bark], Collrepair™ DG [INCI: Hexylene Glycol, Niacin] or Litchiderm [INCI: Litchi *Chinensis* Pericarp Extract] marketed by Laboratoires Sérobiologiques/Cognis/BASF; Argireline® [INCI: Acetyl Hexapeptide-8], Argireline® Amplified [INCI: [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline® [INCI: Acetyl Hexapeptide-30], Aldenine® [INCI: Hydrolized Wheat Protein, Hydrolized Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: *Pseudoalteromonas* Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: *Pseudoalteromonas* Ferment Extract], Hyanify™ [INCI: Saccharide Isomerate], Diffuporine® [INCI: Acetyl Hexapeptide-37], Silusyne® [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39], Adifyline® [INCI: Acetyl Hexapeptide-38], Delisens™ [INCI: Acetyl Hexapeptide-46], Telangyn™ [INCI: Acetyl Tetrapeptide-40], Reproage™ peptide [INCI: Acetyl Hexapeptide-8], Cellynkage™ marine ingredient [INCI: Saccharide Isomerate], Eyedeline™ marine ingredient [INCI: Plankton Extract], Uplevity™ [INCI: Acetyl Tetrapeptide-2], Seacode™ marine ingredient [INCI: *Pseudoalteromonas* Ferment Extract] or Serilesine® peptide solution [INCI: Hexapeptide-10] marketed by Lipotec/Lubrizol; Sirtalice™ [INCI: *Bacillus* Ferment], Epitensive™ [INCI: *Nicotiana Benthamiana* Hexapeptide-40 SH-Oligopeptide-1], Scelleye™ [INCI: *Nicotiana Benthamiana* SH-Oligopeptide-2], Seadermium™ [INCI: Aqua, Glycerin, *Bacillus* Ferment], Pauseile™ [INCI: Aqua, Glycerin, *Bacillus* Ferment] or Neoclair Pro™ [INCI: Aqua, Glycerin, Caprylyl Glycol, Acetyl Tetrapeptide-2] marketed by Lipotrue; Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Quintescine™ IS [INCI: Dipeptide-4], Peptide Vinci 01 [INCI: Penta-decapeptide-1], Peptide Vinci 02™ [INCI: Hexapeptide-3], Aquarize IS™ [INCI: Hydrolyzed Rice Extract], Lanablue [INCI: Algae extract], Ederline™ [INCI: *Pyrus malus* (Apple) Seed Extract], Dynachondrine™ ISR [INCI: Hydrolized Soy Protein], Prolixir S20™ [INCI: Dimer Tripeptide-43], Phytocohesine™ PSP [INCI: Sodium Beta-Sitosteryl Sulfate, Beta-Sitosterol], Perenityl™ IS [INCI: *Pyrus communis* (Pear) Seed Extract], Caspaline 14™ [INCI: Hexapeptide-42], Peptide Q10™ [INCI: Pentapeptide-34 Trifluoroacetate], Survixyl IS™ [INCI: Pentapeptide-31], ChroNOgen™ [INCI: Tetrapeptide-26], Elixiance™ [INCI: *Schinus molle* Extract], Harmoniance™ [INCI: *Nelumbo Nucifera* Flower Extract], Serenityl™ [INCI: Marsdenia Condurango Bark Extract], Natriance™ Wrinkle-less [INCI: Hydrolyzed Corn Protein], Phytoneomatrix™ [INCI: Hydrolyzed Soybean Extract], Prolixir-ICE™ [INCI: Hydrolyzed Rice Protein], PhytoRNx Baobab™ [INCI: Hydrolyzed *Adansonia digitata* Extract], Natriance™ Renovate Extract [INCI: Hydrolyzed Linseed Extract], Natriance Self-Hydrate Extract [INCI: *Pisum sativum* Extract], Actopontine™ YST [INCI: Hydrolyzed Yeast Protein] or Telosense™ [proposed INCI: Hydrolized Soy Protein, Hydrolized Yeast Protein] marketed by Vincience/ISP/Ashland; BONT-L-Peptide [INCI: Palmitoyl Hexapeptide-19], TIM P Peptide [INCI: Acetylhexapeptide-20], ECM Moduline [INCI: Palmitoyl Tripeptide-28], Renaissance™ [INCI: Hydrolyzed Wheat Protein, Palmitoyl Decapeptide-21, Decapeptide-22, Oligopeptide-78, Zinc Palmitoyl Nonapeptide-14] or X50™ Antiaging [INCI: Lactic Acid/glycolic Acid Copolymer, Polyvinyl Alcohol, Copper Palmitoyl Heptapeptide-14, Heptapeptide-15 Palmitate] marketed by Infinitec Activos; EquiStat™ [INCI: *Pyrus malus* Fruit Extract, *Glycine soja* Seed Extract], Juvenesce™ [INCI: Ethoxydiglycol and Caprylic Triglyceride, Retinol, Ursolic Acid, Phytonadione, Ilomastat], Ursolisome™ [INCI: Lecithin, Ursolic Acid, Atelocollagen, Xanthan Gum, Sodium chondroitin sulfate], Basaline™ [INCI: Hydrolyzed Malt Extract], Phytokine [INCI: Hydrolyzed Soy Protein], marketed by Coletica/Engelhard/BASF; Ameliox™ [INCI: Carnosine, Tocopherol, *Silybum marianum* Fruit Extract] or PhytoCellTec *Malus domestica* [INCI: *Malus domestica* Fruit Cell Culture], Lipobelle™ Soyaglycone [INCI: Soy Isoflavones], RoyalEpigen™ P5 [INCI: Butyrospermum Parkii Butter, Hydrogenated Lecithin, Maltodextrin, Pentapeptide-48, Phenethyl Alcohol, Ethylhexylglycerin, Glycerin, Aqua] or DermCom™ [INCI: *Crocus* Chrysanthus Bulb Extract, Acacia Senegal Gum, Aqua/Water] marketed by Mibelle Biochemistry; ActiMatrix™ [INCI: Peptide based mushroom Extract], Peptamide 6 [INCI: Hexapeptide-11] marketed by Active Organics/Arch; and combinations thereof.

The firming agent, skin elasticity agent and/or restructuring agent can be selected, from the group consisting of Argassential™ [INCI: C10-16 Alkyl Glucoside, Dicaprylyl Ether, Glycerin] or Replexium™ BC [INCI: Dimethyl Isosorbide, Polysorbate 20, Aqua, Acetyl Tetrapeptide-11, Acetyl Tetrapeptide-9] marketed by BASF; Prolevis™ [INCI: Hydrolyzed Vegetable Protein] or Poretect™ [INCI: Caprylic/capric Triglyceride, Sorbitan Trioleate, *Apium Graveolens* Seed Extract, *Linum usitatissimum* Seed Extract] marketed by Sederma/Croda; Actifirm™ Ultra Advanced botanical ingredient [INCI: Centella *Asiatica* Extract, *Rosmarinus officinalis* Leaf Extract, Dipropylene Glycol, Alcohol, *Echinacea angustifolia* Leaf Extract] or Actifcol™ Advanced botanical ingredient [INCI: Aqua, Glycerin, Sodium Citrate, Lentinus *Edodes* Extract, Potassium Sorbate, Sodium Benzoate, Phytic Acid] marketed by Lipotec/Lubrizol; Densorphin™ [INCI: Vitex Agnus Castus Extract, Aqua, Maltodextrin] or PhytoCellTec™ Nunatak® [INCI: Isomalt, Aqua, *Saponaria pumila* Callus Culture Extract, Lecithin] marketed by Mibelle; and combinations thereof.

The moisturizing agent can be selected from the group consisting of AquaShuttle™ [INCI: Sorbitol, *Laminaria digitata* Extract, Diatomaceous Earth] marketed by Infinitec; Aqua-Osmoline™ [INCI: *Ceratonia siliqua* (Carob) Seed Extract] marketed by Vincience/ISP/Ashland; Hydralphatine™ Asia [INCI: Hydrogenated Starch Hydrolysate, Panthenol, *Bambusa vulgaris* Shoot Extract, *Nelumbo nucifera* Flower Extract, *Nymphaea alba* Root Extract] or Hydraporine™ [INCI: Betaine, Hydrogenated Lecithin, Honey, Pectin] marketed by Lucas Meyer Cosmetics/Unipex; PatcH2O™ [INCI: Trehalose, Urea, Serine, Glyceryl Polyacrylate, Algin, Sodium Hyaluronate, Pullulan], Aqu'activ™ [INCI: Behenyl Alcohol, Glyceryl Oleate, Cocamide MIPA], Irwinol® [INCI: Octyldodecanol, *Irvingia gabonensis* Kernel Butter, Hydrogenated Coco-Glycerides], Lipodermol®) [INCI: Octyldodecanol, Arachidyl Propionate, Tocopheryl Acetate, Retinyl Palmitate, Ethyl Linoleate, Ethyl Linolenate] or Seanamin® SU [INCI: Sorbitol, Algae Extract, Chondrus *Crispus* (Carrageenan), Fucus Vesiculosus Extract, Algin] marketed by L. Serobiologiques/Cognis/BASF; Snow Algae Powder [INCI: Coenochloris Signiensis Extract] marketed by Mibelle; Hyasol™ BT [INCI: Sodium Hyaluronate], Syn-Up™ [INCI: Benzylsulfonyl D-Seryl Homophenylalanine Amidinobenzamide Acetate] or Pentavitin® [INCI: Saccharide Isomerate] marketed by Pentapharm/DSM; Aqualance™ [INCI: Erythritol, Homarine HCl], Hydraprotectol™ [INCI: Glyceryl Polymethacrylate, Aleuritic Acid, Yeast Extract (Faex), Glycoprotein], Moist 24™ [INCI: *Imperata Cylindrica* Root Extract], Optim Hyal™ [INCI: Hydrolyzed Yeast Extract, Cetyl Hydroxyethylcellulose, Polyglucuronic Acid], Osmocide® 4 [INCI: Glycerin, Acrylates/C10-30 Alkyl Acrylate Crosspolymer] or Revidrate™ [INCI: Ethylhexyl Palmitate, Sorbitan Oleate, Sorbitan Laureate, Myristyl Malate Phosphonic Acid] marketed by Sederma/Croda; Xpertmoist® molecular film [INCI: Glycerin, *Pseudoalteromonas* Ferment Extract, Xanthan Gum, Proline, Alanine, Serine, Ethylhexylglycerin, Caprylyl Glycol] or Actizyme® GL advanced botanical ingredient [INCI: Glycerin, *Mucor miehei* extract, Aqua, Sodium Citrate, Potassium Sorbate, Sodium Benzoate, Phytic Acid] marketed by Lipotec/Lubrizol; and combinations thereof.

The anti-photoaging agent, and/or blue-light protector agent can be selected from the group consisting of Algaktiv™ Genofix CPD [INCI: Plankton Extract, Aqua, Lecithin] marketed by Greenaltech; Blumilight™ Biofunctional [INCI proposed: Water/Aqua (and) Butylene Glycol (and) *Theobroma Cacao* (Cocoa) Seed Extract] marketed by Ashland; Lys'Sun™ [INCI: *Hamamelis virginiana* Leaf Extract, Aqua, Pentylene Glycol, Caprylyl Glycol, Xanthan Gum] marketed by BASF; Vitachelox™ [INCI: *Vitis vinifera* Seed Extract, *Camellia sinensis* Leaf Extract, *Quercus robur* Wood Extract] marketed by Indena; L-VCG™ [INCI: Ascorbyl Glucoside]marketed by Freshine Bio-technology; Lumicease® blue ingredient [INCI: Glycerin, Aqua, Hydrolyzed Pea Protein, Glucose, Sodium Chloride] marketed by Lipotec/Lubrizol; Lightwaves Defense™ [INCI: *Jasminum* Sambac Leaf Cell Extract] marketed by Naolys; Blue Oleoactif™ [INCI: *Glycine soja* Oil, Polyglyceryl-3 Diisostearate, *Oryza sativa* Germ Extract, *Oryza sativa* Extract] marketed by Oleos-Hallstar; Majestem™ [INCI: Glycerin, *Leontopodium alpinum* Callus Culture Extract, Xanthan Gum] or Senestem™ [INCI: Glycerin, *Plantago lanceolata* Leaf Extract, Xanthan Gum] marketed by Sederma; Blueshield™ [INCI: Glycerin, *Capsicum annuum* Fruit Extract, Xanthan Gum] marketed by Solabia; and combinations thereof.

The DNA protecting agent, DNA repair agent, and/or stem cell protecting agent can be selected from the group consisting of; GP4G 5™ [INCI: Aqua, Glycerin, Artemia Extract], Heliostatine [INCI: Aqua, Glycerin, *Pisum Sativum* Extract], Orsirtine [INCI: Aqua, Glycerin, *Oryza sativa* Extract], Chronogen [INCI: Aqua, Butylene Glycol, Tetrapeptide (INCI proposed)], Survixyl IS [INCI: Water, Butylene Glycol, Pentapeptide-31] and Chrondricare™ [INCI: Aqua, Butylene Glycol Pentapeptide-28] marketed by Vincience/ISP/Ashland; Lanacityn® [INCI: Glycerin, Aqua, *Alteromonas ferment* extract, *Chrysanthellum indicum* extract] or Melinoil™ [INCI: Isopropyl Palmitate, Lecithin, Aqua, Acetyl Hexapeptide-1] marketed by Atrium Innovations/Lucas Meyer Cosmetics; Repair Complex™ [INCI: *Bifida* Ferment Lysate] marketed by CLR; Phycojuvenine™ [INCI: *Laminaria digitata*] marketed by Codif; Unirepair™ T-43 [INCI: Butylene Glycol, Acetyl Tyrosine, Proline, Hydrolyzed Vegetable Protein, Adenosine Triphosphate] marketed by Induchem; Dragosine™ [INCI: Carnosine] marketed by Symrise; DN-Age™ [INCI: *Cassia Alata* Leaf Extract] marketed by Laboratories Serobiologiques/Cognis/BASF; Helioguard™ [INCI: *Porphyra umbilicalis* encapsulated into liposomes], PhytoCellTec™ *Malus Domestica* [INCI: PhytoCellTec *Malus Domestica*] or PhytoCellTec™ Argan [INCI: Argania *Spinosa* Sprout Cell Extract, Isomalt, Lecithin, Sodium Benzoate, Aqua] marketed by Mibelle Biochemistry; Pepha-Protect™ [INCI: Water Melon Extract] marketed by Pentapharm/DSM; Celligent™ [INCI: *Helianthus annuus* Seed Oil, Ethyl Ferulate, Polyglyceryl-5 Trioleate, *Rosmarinus officinalis* Leaf Extract, Aqua, Disodium Uridine Phosphate] or Defensil™ [INCI: Octyl Dodecanol, Echium Plantagineum Seed Oil, Cardiospermum Halicacabum Extract, *Helianthus annuus* Seed Oil Unsaponifiables] marketed by Rahn; Venuceane™ [INCI: *Thermus thermophilus* Ferment, Glycerin], UV-Soft™ [INCI: Yeast Extract], Renovage [INCI: Caprylic/Capric Triglyceride, Teprenone], Juvinity™ [INCI: Caprylic/Capric Triglyceride, Geranylgeranyl propanol (proposed)], Phytessence™ Holyherb [INCI: Butylene Glycol, *Eriodictyon californicum* (Holyherb) Flower/Leaf/Stem Extract] or Resistem™ [INCI: Glycerin, *Globularia cordifolia* Ferment] marketed by Sederma/Croda; Infraguard™ [INCI: *Caesalpinia spinosa* Fruit Pod Extract, Propylene Glycol, Aqua, *Helianthus annuus* Sprout Extract, Sodium Benzoate, Phenoxyethanol] marketed by Mibelle; Heliomoduline™ [INCI: Low molecular weight peptides from cottonseed] or Stem-C-Guard™ [Hydrolyzed Pea] marketed by Silab; and combinations thereof.

The reactive carbonyl species scavenger, free radical scavengers and/or anti-glycation agent, detoxifying agent, antioxidant and/or anti-pollution agent can be selected, for example and not restricted to, from the group formed by carnosine and its derivatives; GHK [INCI: Tripeptide-1] and its salts and/or derivatives or Quintescine™ IS [INCI: Dipeptide-4] marketed by Vincience/ISP/Ashland; Preregen [INCI: *Glycine Soja* (Soybean) Protein, Oxido Reductases], Edelweiss GC [INCI: *Leontopodium alpinum* Extract], Lipogard™ [INCI: Squalane, Ubiquinone], Nectapure™ [INCI: *Buddleja davidii* Extract, *Thymus vulgaris* Extract], Alpaflor™ Nectapure [INCI: *Buddleja davidii* Extract, *Thymus vulgaris* Extract, Glycerin, Water] or Dismutin-BTT™ [INCI: Highly purified SOD from a natural yeast strain of *Saccharomyces cerevisiae*] marketed by Pentapharm/DSM; Preventhelia® [INCI: Diaminopropionoyl Tripeptide-33], Aldenine® [INCI: Hydrolyzed Wheat Protein, Hydrolyzed Soy Protein, Tripeptide 1], Lipochroman™ [INCI: Dimethylmethoxy Chromanol], Thermostressine® [INCI: Acetyl Tetrapeptide-22] Pollushield™ functional ingredient [INCI: Diisopropyl Adipate, Lecithin, Acrylic Acid/Acrylamidomethyl Propane Sulfonic Acid Copolymer, Dimethylmethoxy Chromanol, Xanthan Gum] or Bodyfensine® [INCI: Acetyl Dipeptide-3 Aminohexanoate] marketed by Lipotec/Lubrizol; Unactyl™ [INCI: Mannitol, *Pisum sativum* Extract, Histidine HCl, Arginine, Cyclodextrin, Dextrin, Yeast Extract, Acetyl Tyrosine, Pyridoxine HCl, Khaya *Senegalensis* Bark Extract, Nicotinamide, Adenine Dinucleotide, Disodium Succinate, Aspartic Acid], Imidinyl™ [INCI: Tamarindus Indica Seed Polysaccharide], Phystrogene™ [INCI: Butylene Glycol, *Malva sylvestris* (Mallow) Extract, Xanthan Gum] or Purisoft™ [INCI: Moringa Pterygosperma Seed Extract] marketed by Laboratoires Sérobiologiques/Cognis/BASF; AquaCacteen™ [INCI: Glycerin, Opuntia *Ficus* Indica Stem Extract, Phenoxyethanol, Aqua], Trimoist™ (KM F) [INCI: Sodium Stearoyl Lactylate, Cetyl alcohol, Olus Vegetable oil, Tocopheryl acetate, Glycerin, *Glycine soja* sterol, Sodium lactate, Sodium carboxymethyl betaglucan, Carnosine, Lactic Acid], MelanoBronze™ [INCI: Vitex Agnus Castus Extract (Monk's pepper berries extract (phyto-endorphins)), Acetyl Tyrosine], CM-Glucan™ [INCI: Sodium Carboxymethyl Betaglucan, Phenoxyethanol, SunActin™ [INCI: *Helianthus annuus* (Sunflower) Sprout Extract, Tocopherols, Glycerin, Lecithin, Phenoxyethanol, Aqua], GSP-T™ skin [INCI: Glycerin, Alcohol, Aqua, PEG-40 Hydrogenated Castor Oil, *Vitis vinifera* (Grape) Seed Extract] or Detoxophane™ [INCI: *Lepidium sativum* Sprout Extract, Lecithin, Phenoxyethanol, Glycerin, Water] marketed by Mibelle Biochemistry; Bacocalmine™ [INCI: PEG-8, Bacopa Monnieri Extract, Water (Aqua), Hydroxyethylcellulose], Kombuchka™ [INCI: *Saccharomyces/Xylinum* Black Tea Ferment, Glycerin, Hydroxyethyl cellulose], Citystem™ [INCI: Glycerin, *Marrubium vulgare* Extract] or Prodizia™ [INCI: *Albizia julibrissin* Extract, Glycerin] marketed by Sederma/Croda; Extramel™ C [INCI: Hydroxypropyltrimonium Maltodextrin Crosspolymer, *Cucumis melo* (Melon) Fruit Extract] marketed by Seppic; Defensine™ [INCI: *Triticum Vulgare* Germ Extract], Apolluskin® [INCI: *Taraxacum officinale* (Dandelion) Extract], Detoxyl® [INCI: Water, Butylene Glycol, Butyrospermum parkii (Shea Butter) Seedcake Extract] or Antiglyskin™ [INCI: Aqua, *Helianthus annuus* Seed Extract] marketed by Silab; and combinations thereof.

The personal care formulation may include agents which increase the percutaneous absorption of any active compounds present therein. Such agents include, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others.

The personal care formulation according to the invention is also suitable for sunscreen or sun care products. Thus, the personal care formulation may include ingredients typically used for sunscreening purposes. Non-limiting examples include benzoic acid derivatives, para-aminobenzoic acid (PABA), in particular the monoglycerol esters of PABA, the ethyl esters of N, N-propoxy PABA, the ethyl esters of N, N-diethoxy PABA, the ethyl esters of N, N-dimethyl PABA, the esters methyl, N, N-dimethyl PABA, butyl esters of N, N-dimethyl PABA; anthranilic acid derivatives such as homomenthyl-N-acetyl anthranilate; salicylic acid derivatives such as amyl salicylate, homomenthyl salicylate, ethylhexyl salicylate, phenyl salicylate, benzyl salicylate, (p-isopropanol phenyl salicylate); cinnamic acid derivatives such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate, (p-methoxy 2-ethylhexyl) cinnamate, (p-methoxy 2-ethoxy ethyl) cinnamate, (p-methoxy cyclohexyl) cinnamate, ethyl-ocyano-3-phenyl cinnamate, (2-ethyl hexyl)-o cyano-3-phenyl cinnamate, glyceryl diparamethoxy mono-2-ethylhexanoyl cinnamate; the family of benzophenone derivatives such as 2,4-dihydroxy benzophenone, 2,2'-dihydroxy 4-methoxy benzophenone, 2,2',4,4'-tetrahydroxy benzophenone, 2-hydroxy 4-methoxy benzophenone, 2-hydroxy 4-methoxy 4'-methyl benzophenone, 2-hydroxy 4-methoxy benzophenone-5-sulfonate, 4-phenyl benzophenone, (2-ethyl hexyl) 4'-phenyl benzophenone-2-carboxylate, 2-hydroxy 4-(n-octyloxy) benzophenone, 4-hydroxy 3-carboxy benzophenone; 3-(4'-methyl benzylidene)d, l-camphor, 3-(benzylidene)-d, l-camphor, benzalkonium methosulfate camphor; urocanic acid, ethyl urocanate; sulfonic acid derivatives such as 2-phenyl benzimidazole-5 sulfonic acid and its salts; the family of triazine derivatives such as hydroxyphenyl triazine, (ethylhexyloxy) (hydroxyphenyl) (4-methoxy phenyl) triazine, 2,4,6-trianilino-(p-carbo-2'-ethylhexyl-1'-oxy)-1,3,5-triazine, 4,4-((6-((((1,1-dimethyl ethyl) amino) carbonyl) phenyl) amino)-1,3,5-triazine-2,4-diyl diimino) bis(2-ethyl hexyl) ester of benzoic acid, 2-phenyl-5-methyl benzoxazole, 2-(2'-hydroxy 5'-methyl phenyl) benzotriazole, 2-(2'-hydroxy 5'-t-octyl phenyl) benzotriazole, 2-(2'-hydroxy 5'-methyl phenyl) benzotriazole; dibenzazine; dianisoylmethane, 4-methoxy-4'''-t-butyl benzoyl methane; 5-(3,3-dimethyl 2-norbornylidene)-3-pentan-2-one; diphenylacrylate derivatives such as (2-ethylhexyl) 2-cyano 3,3-diphenyl 2-propenoate, ethyl-2-cyano 3,3-diphenyl 2-propenoate; polysiloxanes such as benzylidene siloxane malonate; inorganic solar filters, also called "mineral screens" such as titanium oxides, zinc oxides, cerium oxide, zirconium oxide, yellow, red or black iron oxides, chromium oxides.

The personal care formulation of the invention may include deodorant agents such as for example, but not limited to, alkali silicates, zinc salts such as zinc sulfate, gluconate zinc, zinc chloride, zinc lactate; quaternary ammonium salts such as cetyltrimethylammonium salts, cetylpyridinium salts; sodium bicarbonate; cyclodextrins; metallic zeolites; aluminum hydrobromide, aluminum hydrochlorides, aluminum chloride, aluminum sulfate, aluminum and zirconium hydrochlorides, aluminum and zirconium hydrochloride, aluminum and zirconium tetrachloride, aluminum and zirconium pentachlorohydrate, aluminum and zirconium octochlorohydrate, aluminum sulfate, sodium and aluminum lactate, aluminum hydrochloride and glycol complexes, such as aluminum hydrochloride and propylene glycol, aluminum dihydrochloride and propylene glycol complex, aluminum sesquichlorohydrate and propylene glycol complex, aluminum hydrochloride and polyethylene glycol complex, dihydrochloride complex aluminum and polyethylene glycol, the complex of aluminum sesquichlorohydrate and polyethylene glycol.

The personal care formulation of the invention may include film former ingredients such as for example, but not limited to, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

The personal care formulation of the invention may include insect repellents such as for example, but not limited N,N-diethyl-m-toluamide, pentane-1,2-diol, Ethyl Butylacetylaminopropionate, essential oils and similar compounds.

The invention is illustrated by the following non-limiting examples.

EXAMPLES

Example 1

Stability of Emulsions Comprising MCC and Natural Gums

To test the efficacy of natural polymeric emulsifiers, different emulsions were prepared combining MCC, NaCMC and/or natural gums. Phenoxyethanol, MCC, NaCMC and natural gums were added to water and, after that, the oil phase was added to the water phase, slowly under stirring.

After that, shear was increased to 10.000 rpm for 1 minute with an Ultra-Turrax™ disperser. pH was adjusted to 5.5. This process was carried out under both cold and hot process (heating at 70° C. during the emulsification process) conditions shown in TABLES 1 and 2.

TABLE 1

| Ingredient | Concentration (%, w/w) | | | |
|---|---|---|---|---|
| Deionized water | 78.80 | 78.80 | 78.80 | 78.80 |
| Phenoxyethanol | 0.50 | 0.50 | 0.50 | 0.50 |
| MCC | 0.42 | 0.42 | 0.42 | 0.42 |
| NaCMC | 0.08 | 0.08 | 0.08 | 0.08 |
| Tara gum | 0.20 | 0.20 | | |
| Guar Gum | | | 0.20 | 0.20 |
| Caprylic/capric triglycerides | 20.00 | 20.00 | 20.00 | 20.00 |
| PROCESS | Cold | Hot | Cold | Hot |
| VISCOSITY (mPa · s)@20rpm | 770 | 685 | 820 | 860 |
| YIELD (dyn/cm$^2$) | 27 | 16 | 72 | 30 |
| COALESCENCE (AU) | 3.5 | 3.5 | 4 | 3.5 |
| STABILITY (1 MONTH, 50° C.) | FAIL | FAIL | FAIL | FAIL |

TABLE 2

| Ingredient | Concentration (%, w/w) | | | | | | |
|---|---|---|---|---|---|---|---|
| Deionized water | 78.80 | 79.00 | 79.00 | 78.80 | 78.80 | 78.80 | 78.80 |
| Phenoxyethanol | 0.50 | 0.50 | 0.50 | 0.50 | 0.50 | 0.50 | 0.50 |
| MCC | | 0.42 | 0.42 | 0.60 | 0.60 | 0.42 | 0.42 |
| NaCMC | | 0.08 | 0.08 | 0.10 | 0.10 | 0.08 | 0.08 |
| Diutan gum | 0.20 | | | | | 0.20 | 0.20 |
| Caprylic/capric triglycerides | 20.00 | 20.00 | 20.00 | 20.00 | 20.00 | 20.00 | 20.00 |
| PROCESS | Cold | Cold | Hot | Cold | Hot | Cold | Hot |
| VISCOSITY (mPa · s)@20 rpm | 675 | 210 | 180 | 400 | 285 | 1365 | 1280 |
| YIELD (dyn/cm$^2$) | 65 | 4 | 16 | 17 | 3 | 205 | 116 |
| COALESCENCE (AU) | 2.5 | 3.5 | 4 | 3.5 | 2.5 | 4.5 | 4.5 |
| STABILITY (1 MONTH, 50° C.) | FAIL | FAIL | FAIL | FAIL | FAIL | PASS | PASS |

Viscosity was measured by was measured at 25° C. with a Brookfield LVT viscometer using an appropriate spindle depending on the viscosity of the emulsion. The emulsion was tested at 20 rpm, and viscosity determined at 24 h after the emulsion was prepared. Results are quoted in mPa·s.

Yield value is commonly defined as initial resistance to flow under applied stress. In the case of Bingham and Ellis plastic flow, a minimum shear stress is required to initiate flow. This minimum stress is known as the yield value or yield index. The yield is measured by Brookfield Viscometry Method by determining the viscosity at 0.5 and 1 rpm at 25° C. The Brookfield yield values is calculated as Brookfield Yield Value=(Apparent Viscosity at 0.5 rpm−Apparent Viscosity at 1 rpm)/100 and is measured in dyn/cm$^2$.

Coalescence is a measure of emulsion stability. Coalescence was measured by visual inspection wherein results are values from a scale of from 0 to 5 (with 5 being the best result of no coalescence and 0 being the worst result of complete phase separation). A value of 0 represents an appearance of thick film layer of oil in the surface (i.e., a broken emulsion); 1 accounts for a slight film layer; 2 accounts for oil pooling; 3 accounts for numerous small and large droplets; 4 accounts for a few small droplets; and 5 accounts for no visible droplets.

In Tables 1 and 2, FAIL means that the emulsions were not stable after 1 month at 50° C.; PASS: stable after 1 month at 50° C.

The results show that there is a surprisingly synergistic effect between diutan gum when combined with MCC and NaCMC, both in viscosity and yield. Additionally, to higher viscosity and yield, the emulsion with the mixture of MCC, NaCMC and diutan gum gave better results in coalescence after 24 hours at 50° C., so the stability of the emulsion is higher. None of the other natural gums provided satisfactory results as none of them were stable after a period of a month at 50° C.

Example 2

Polymers Ratio Determination and Concentration Influence

O/W emulsions were prepared as in EXAMPLE 1 but different concentrations of components were tested, as shown in TABLE 3.

TABLE 3

| Ingredient | Concentration (%, w/w) | | | | | | | | |
|---|---|---|---|---|---|---|---|---|---|
| Diutan Gum | 0.70 | 0.60 | 0.50 | 0.40 | 0.35 | 0.30 | 0.20 | 0.10 | 0.00 |
| MCC | 0.00 | 0.08 | 0.16 | 0.25 | 0.30 | 0.34 | 0.42 | 0.48 | 0.60 |
| NaCMC | 0.00 | 0.02 | 0.04 | 0.05 | 0.05 | 0.06 | 0.08 | 0.12 | 0.10 |
| VISCOSITY (mPa · s)@20 rpm | 2490 | 2140 | 1880 | 1650 | 1575 | 1510 | 1365 | 1150 | 400 |
| YIELD (dyn/cm$^2$) | 266 | 223 | 188 | 185 | 191 | 213 | 205 | 149 | 17 |
| COALESCENCE (A.U., 1 MONTH, 50° C.) | 2.5 | 2.5 | 3 | 3.5 | 3.5 | 3.5 | 4 | 2.5 | 2.5 |

The emulsions with coalescence results of 3 or more were considered to be the best performing emulsions. Based on a ratio of components similar to those of the best performing emulsions, the effect of the overall concentration of diutan, MCC and NaCMC was tested as shown in TABLE 4.

TABLE 4

| Ingredient | Concentration (%, w/w) | | | | | |
|---|---|---|---|---|---|---|
| Diutan Gum | 0.14 | 0.17 | 0.2 | 0.23 | 0.26 | 0.29 |
| MCC | 0.30 | 0.36 | 0.42 | 0.48 | 0.54 | 0.60 |
| NaCMC | 0.06 | 0.07 | 0.08 | 0.09 | 0.10 | 0.11 |
| % Total concentration (w/w) | 0.50 | 0.60 | 0.70 | 0.80 | 0.90 | 1.00 |
| VISCOSITY (mPa · s) @20 rpm | 840 | 1100 | 1365 | 1545 | 1790 | 2025 |
| YIELD (dyn/cm$^2$) | 114 | 208 | 226 | 254 | 331 | 386 |
| COALESCENCE (A.U., 24 hours, 25° C.) | 4 | 4.5 | 4.5 | 4.5 | 4.5 | 5 |
| COALESCENCE (A.U., 1 MONTH, 50° C.) | 2.5 | 2.5 | 4.0 | 3.0 | 3.0 | 3.0 |

The higher the total concentration of the combination, the higher the viscosity at both room temperature and 50° C. Regarding coalescence, the optimal concentration of the emulsifier composition comprising diutan gum, MCC and NaCMC was 0.7% by weight based on the total weight of the composition.

Example 3

Surface Tension Measurement

Six-hundred (600) gram batches of water containing either diutan gum or MCC in combination with NaCMC at 0.01 wt %, were prepared in an 800 mL beaker using a 2 inch marine blade. The batches were mixed for one hour at 300 rpm (to avoid splashing).

Viscosity was recorded 24 hours later using a Brookfield Viscometer and spindle #1. Samples were run on a Kruss Tensiometer for 60 minutes with data points every 30 seconds.

The definition of a "surface active agent" is given in the World Customs Organization-Explanatory Notes and can be found in the chapter notes of chapter 34 of the tariff.

Under heading 34.02 of said chapter, "organic surface-active agents" are products which when mixed with water at a concentration of 0.5 percent at 20° C. and left to stand for one hour at the same temperature:

(a) give a transparent or translucent liquid or stable emulsion without separation of insoluble matter; and
(b) reduce the surface tension of water to 45 mN/m (45 dyne/cm) or less.

The surface tension obtained for:

Diutan Gum at 0.01 wt % in water was 62.069 mN/m, with a first value of 57.51 mN/m; and MCC+CMC at 0.01 wt % was 60.033 mN/m, with a first value of 52.56 mN/m.

As the surface tension was higher than 45 mN/m, these ingredients are not considered as surface active agents.

Example 4

Co-Emulsifiers Effect

The effect of a co-emulsifier was investigated, as shown in TABLE 5. Glyceryl Caprylate and Polyglyceryl-3 Laurate were each added to an emulsion in an amount of 0.5% by weight. In each case, there was a slight increase in emulsion stability, especially with Polyglyceryl-3 Laurate (which gave an emulsion with a coalescence value of 5 after 4 weeks at 50° C.). When each of the co-emulsifiers was used alone in the emulsion, i.e., in the absence of MCC, NaCMC and Diutan gum, after 24 hours there was complete separation. This indicates that the use of at least MCC and Diutan Gum is mandatory for a good stability.

TABLE 5

| Ingredient | Concentration (%, w/w) | | | |
|---|---|---|---|---|
| Deionized water | Qs100 | Qs100 | Qs100 | Qs100 |
| Phenoxyethanol | 0.50 | 0.50 | 0.50 | 0.50 |
| MCC | 0.42 | 0.42 | | |
| NaCMC | 0.08 | 0.08 | | |
| Diutan gum | 0.20 | 0.20 | | |
| Glyceryl Caprylate | 0.5 | | 0.5 | |
| Polyglyceryl-3 Laurate | | 0.5 | | 0.5 |
| Caprylic/capric triglycerides | 20.00 | 20.00 | 20.00 | 20.00 |
| PROCESS | Cold | Cold | Cold | Cold |
| VISCOSITY (mPa · s)@20 rpm | 1440 | 1395 | — | — |
| COALESCENCE (AU) | 5 | 5 | 0 | 0 |
| STABILITY (1 MONTH, 50° C.) | PASS | PASS | FAIL | FAIL |

Example 5

Shear Impact in Polymer Properties

The influence of shear was investigated. Some polymers are affected by shear, by losing some of their properties. For this reason, it is important to understand if the application of shear can modify the properties of the emulsifier compositions of the invention. A mucilage containing 0.2% Diutan Gum, 0.42% MCC and 0.08% CMC by weight was stirred with an Ultra-Turrax™ disperser at different speeds during 10 mins. Viscosity and yields were measured after 24 hours and results noted in Table 6.

TABLE 6

| Ingredient | Concentration (%, w/w) | | | |
|---|---|---|---|---|
| Deionized water | Qs100 | Qs100 | Qs100 | Qs100 |
| MCC | 0.42 | 0.42 | 0.42 | 0.42 |
| NaCMC | 0.08 | 0.08 | 0.08 | 0.08 |
| Diutan gum | 0.20 | 0.20 | 0.20 | 0.20 |
| PROCESS (rpm, 10 mins) | 0 | 3000 | 5000 | 10000 |
| VISCOSITY (mPa · s)@20 rpm | 1450 | 1355 | 1440 | 1395 |
| YIELD (dyn/cm$^2$) | 220 | 206 | 207 | 227 |

Shear does not have any impact on the effect of the emulsifier system of the invention.

Example 6 pH Compatibility

Different emulsions at different pH were prepared and their properties were analyzed as shown in TABLE 7.

TABLE 7

| Ingredient | Concentration (%, w/w) | | | | |
|---|---|---|---|---|---|
| Deionized water | Qs100 | Qs100 | Qs100 | Qs100 | Qs100 |
| Phenoxyethanol | 0.50 | 0.50 | 0.50 | 0.50 | 0.50 |
| MCC | 0.42 | 0.42 | 0.42 | 0.42 | 0.42 |
| NaCMC | 0.08 | 0.08 | 0.08 | 0.08 | 0.08 |
| Diutan gum | 0.20 | 0.20 | 0.20 | 0.20 | 0.20 |
| Caprylic/capric triglycerides | 20.00 | 20.00 | 20.00 | 20.00 | 20.00 |
| pH | 4 | 5.5 | 6 | 7 | 8 |
| VISCOSITY (mPa · s)@20 rpm | 1610 | 1450 | 1450 | 1255 | 1460 |
| YIELD (dyn/cm$^2$) | 263 | 220 | 233 | 159 | 200 |

The emulsion was stable at all pH after 24 hours with a slight decrease in the yield when increasing the pH.

Example 7

Viscosity Boost

The addition of a starch derivative to boost emulsion viscosity was also investigated. Aa drawback of biopolymers is that they do not provide thick emulsions. Thick emulsions are required in order to obtaining gel cream or cream products.

Four formulations labelled A, B, C and D were prepared, and viscosity and yield were measured for each formulation, as detailed in TABLE 8.

TABLE 8

| | Concentration (%, w/w) | | | | |
|---|---|---|---|---|---|
| Ingredient | A | B | C | D | E |
| Deionized water | Qs100 | Qs100 | Qs100 | Qs100 | Qs 100 |
| Phenoxyethanol | 0.50 | 0.50 | 0.50 | 0.50 | 0.50 |
| MCC | 0.42 | 0.42 | 0.42 | 0.42 | — |
| NaCMC | 0.08 | 0.08 | 0.08 | 0.08 | |
| Diutan gum | 0.20 | 0.20 | 0.20 | 0.20 | — |
| Polyglyceryl-3 Laurate | — | 0.50 | — | 0.50 | — |
| Starch derivative | — | — | 0.30 | 0.30 | 0.70 |
| Caprylic/capric triglycerides | 20.00 | 20.00 | 20.00 | 20.00 | 20.00 |
| pH | 5.5 | 5.5 | 5.5 | 5.5 | 5.5 |
| VISCOSITY (mPa · s)@20 rpm | 1450 | 1450 | 2955 | 2815 | 2260 |
| YIELD (dyn/cm$^2$) | 220 | 216 | 482 | 404 | 147 |

The addition of a starch derivative enables the preparation of gel cream emulsions or cream emulsions whereas only fluid emulsion (lotions) are obtained when starch derivatives are not present.

Example 8

Performance in High-Oil O/W Emulsions

O/W emulsions were prepared using different concentrations of emulsifier and oil. The composition of the emulsions was as shown in TABLE 9.

TABLE 9

| Ingredient | % (w/w) |
|---|---|
| Deionized water | QSP |
| Phenoxyethanol | 0.50 |
| Emulsifier (MCC + NaCMC + Diutan gum in a ratio of 5.25:1:2.5, w/w) | 0.5-1.0 |
| Caprylic capric triglyceride | 10-50 |
| Citric acid | Qs to PH 5.5 |

The viscosity results of the formulations after 24 hours 25° C. in mPa·s at 20 rpm are summarized in Table 10.

TABLE 10

| | | Emulsifier (%, w/w) | | | | | |
|---|---|---|---|---|---|---|---|
| | | 0.5 | 0.6 | 0.7 | 0.8 | 0.9 | 1.0 |
| Oil concentration (%, w/w) | 10 | 720 | 885 | 1005 | 1230 | 1380 | 1585 |
| | 20 | 840 | 1100 | 1450 | 1545 | 1790 | 2025 |
| | 30 | 1240 | 1580 | 1960 | 2120 | 2405 | 2745 |
| | 40 | 1760 | 2130 | 2695 | 2950 | 3455 | 3755 |
| | 50 | 2455 | 2985 | 3610 | 4400 | 5340 | 5430 |

The emulsifier comprising MCC+NaCMC+Diutan gum shows low viscosity and good stability at all concentrations tested, including high concentrations of oil. Good stability means that viscosity does not differ more than 30%, pH does not differ more than 1 point and the coalescence ratio is acceptable (above 3 over a scale from 0 to 5), compared to initial time.

Example 9

Stability at Different pH Values Over Time

Emulsions were prepared having the ingredients shown in TABLE 11.

TABLE 11

| Ingredient | % (w/w) |
|---|---|
| Deionized water | QSP |
| Phenoxyethanol | 0.50 |
| Emulsifier (MCC + NaCMC + Diutan gum in a ratio of 5.25:1:2.5, w/w) | 0.70 |
| Caprylic capric triglyceride | 20.00 |

Citric acid was added to adjust the pH to values ranging from 3 to 6, and sodium hydroxide to adjust the pH to 7 or 8.

Viscosity results are summarized in TABLE 12.

TABLE 12

| | pH 3 | pH 4 | pH 5 | pH 6 | pH 7 | pH 8 |
|---|---|---|---|---|---|---|
| Viscosity (mPa · s) at 24 hrs (room temperature) at 20 rpm | 1730 | 1610 | 1450 | 1450 | 1255 | 1460 |
| Viscosity (mPa · s) at 1 month 50° C. at 20 rpm | 1710 | 1800 | 1485 | 1585 | 1380 | 1580 |

After 1 month at 50° C., viscosity maintained between a very small variation range, less than 30%, pH does not differ more than 1 point and the coalescence ratio is acceptable (above 3 over a scale from 0 to 5), which allows formulators to work at different pHs.

Example 10

Tolerance to Ethanol

Using ethanol in cosmetics products is common to bring freshness sensation to the consumer and speed up the drying time leading to a faster absorbency of the product on the skin. Nevertheless, some natural ingredients are not tolerant to ethanol.

The formulations shown in TABLE 13 containing ethanol were prepared and viscosity determined at 20 rpm:

TABLE 13

| Ingredient | % (w/w) | % (w/w) | % (w/w) | % (w/w) | % (w/w) |
|---|---|---|---|---|---|
| Deionized water | QSP | QSP | QSP | QSP | QSP |
| Phenoxyethanol | 0.50 | 0.50 | 0.50 | 0.50 | 0.50 |
| (MCC + NaCMC + Diutan gum in a ratio of 5.25:1:2.5, w/w) | 0.70 | 0.70 | 0.70 | | |
| Tara Gum | | | | 1 | 1 |
| Caprylic capric triglyceride | 20.00 | 20.00 | 20.00 | 0 | 0 |
| Ethanol | 0 | 5 | 10 | 5 | 10 |
| Citric acid | Qs to pH 5.5 | Qs to pH 5.5 | Qs to pH 5.5 | 0 | 0 |
| VISCOSITY (mPa · s)@20rpm | 1450 | 1490 | 1635 | 4600 | 9650 |
| Aspect | Smooth homogeneous gel | Smooth homogeneous gel | Smooth homogeneous gel | Smooth homogeneous gel | Structured and lumpy gel |

When using an emulsifier comprising MCC+NaCMC+Diutan gum there were no significant changes in viscosity, pH and coalescence ratio, meaning that the emulsions were stable. In contrast, when tara gum was used, viscosity was very high at concentration of 5 and 10% (w/w) of ethanol and the gel aspect at 10% ethanol was not satisfactory.

Example 11

Purifying Serum for Oily Skin

In a clean beaker, ingredients of phase A are mixed together under stirring.

Then B is added under stirring (dispersion blade) until homogeneous blend is obtained.

Then C is prepared in another beaker and added to batch little by little under strong stirring and then the emulsion is homogenized for 1 minute at 10,000 rpm with a rotor stator.

Then ingredients of phase D are added one by one to batch under stirring. TABLE 14 shows the formulation.

TABLE 14

| | Ingredient | % (w/w) |
|---|---|---|
| A | Deionized water | QSP |
| | Glycerin | 2.00 |
| | Propanediol | 3.00 |
| | Polyglyceryl-3 Laurate | 0.50 |
| | Phenoxyethanol | 0.50 |
| B | MCC | 0.42 |
| | NaCMC | 0.08 |
| | Diutan gum | 0.20 |
| C | Isostearyl Isostearate | 5.00 |
| | Ethylhexyl cocoate | 15.00 |
| | Fragrance | 0.20 |
| D | Ethanol | 2.00 |
| | Grapefruit seed extract | 2.00 |

Example 12

Diaper Rash Lotion

In a clean beaker, ingredients of phase A are mixed under stirring. Then B is added under stirring (dispersion blade) until homogeneous. Then C is added to batch under rotor stator homogenization until the pigment is fully dispersed. Then D is prepared in another beaker and added to batch little by little under strong stirring. Then, the emulsion is homogenized for 1 minute at 10,000 rpm with a rotor stator. Finally, phase E is added under stirring. TABLE 15 shows the formulation.

TABLE 15

| | Ingredient | % |
|---|---|---|
| A | Deionized water | QSP |
| | Glycerin | 5.00 |
| | Propanediol | 3.00 |
| | Polyglyceryl-3 Laurate | 0.50 |
| | Phenoxyethanol | 0.50 |
| B | MCC | 0.48 |
| | NaCMC | 0.09 |
| | Diutan gum | 0.23 |
| C | Zinc oxide | 10.00 |
| D | Almond oil | 30.00 |
| E | Chamomile extract | 2.00 |

In a clean beaker, ingredients of phase A are mixed under stirring. Then B is added under stirring (dispersion blade) until homogeneous dispersion. Then C is added to batch under rotor stator homogenization until the pigment is fully dispersed. Then D is prepared in another beaker and added to batch little by little under strong stirring then the emulsion is homogenized for 1 minute at 10,000 rpm with a rotor stator. Then phase E is added under stirring.

Example 13

Sun Care Lotion SPF50

In a clean beaker, ingredients of phase A are mixed under stirring.

Then B is added under stirring (dispersion blade) until homogeneous dispersion while heating up to 75° C. Then C is added to batch. Then D is prepared in another beaker by mixing the ingredients together and heating up to 75° C. then D is added to batch little by little under strong stirring. Subsequently, the emulsion is homogenized for 1 minute at 10,000 rpm with a rotor stator. Finally, the emulsion is cooled down under stirring to 30° C. for the addition of E. TABLE 16 shows the formulation.

TABLE 16

| | Ingredient | % |
|---|---|---|
| A | Deionized water | QSP |
| | Glycerin | 3.00 |
| | Polyglyceryl-3 Laurate | 0.50 |
| B | MCC | 0.42 |
| | NaCMC | 0.08 |
| | DG | 0.20 |
| C | Sodium stearoyl glutamate | 0.20 |
| D | Bis-ethylhexyloxyphenol methoxyphenyl triazine | 3.00 |
| | Butyl methoxydibenzoylmethane | 3.50 |
| | Ethylhexyl salicylate | 5.00 |
| | Octocrylene | 10.00 |
| | Ethylhexyl triazone | 2.50 |
| | Caprylic/capric triglyceride | 5.00 |
| | Diisopropyl sebacate | 9.00 |
| E | Phenylpropanol, Hexylene glycol | 0.80 |
| | Methylene bis-benzotriazolyl tetramethylbutylphenol | 6.00 |
| | Citric acid 10% in water | 0.08 |

The invention claimed is:

1. An emulsifier composition comprising:

a) from 30 to 75 wt. % of microcrystalline cellulose;

b) from 20 to 75 wt. % of at least one biogum of microbial origin; and c) from 5 to 15 wt. % of at least one cellulose ether or derivative thereof selected from the group consisting of methyl cellulose, ethyl cellulose, hydroxyethyl cellulose, hydroxyethylmethyl cellulose, methylhydroxyethyl cellulose, hydroxypropyl cellulose, hydroxypropylmethyl cellulose, carboxymethyl cellulose, sodium carboxymethyl cellulose, and mixtures thereof, wherein all weight percentages are based on the total weight of the emulsifier composition;

wherein the at least one biogum of microbial origin comprises diutan gum; and wherein the weight ratio of (a):(b):(c) is from 3 to 6 (a), from 1 to 10 (b), and (c) is 1.

2. The emulsifier composition of claim 1, wherein the microcrystalline cellulose is from 40 wt. % to 70 wt. % of the emulsifier composition.

3. The emulsifier composition of claim 1, wherein the at least one biogum of microbial origin is from 25 wt. % to 45 wt. % of the emulsifier composition.

4. The emulsifier composition of claim 1, wherein the weight ratio of (a):(b):(c) is from 4 to 5.5 (a), from 1 to 3.5 (b), and (c) is 1.

5. The emulsifier composition of claim 1, wherein the at least one cellulose ether or derivative thereof comprises sodium carboxymethyl cellulose.

6. The emulsifier composition of claim 1, wherein the at least one biogum of microbial origin is from 25 wt. % to 35 wt. % of the emulsifier composition.

7. The emulsifier composition of claim 1, wherein the at least one cellulose ether or derivative thereof is from 8 wt. % to 12 wt. %.

* * * * *